(12) United States Patent
Smith

(10) Patent No.: US 7,573,039 B2
(45) Date of Patent: Aug. 11, 2009

(54) COMPTON CAMERA CONFIGURATION AND IMAGING METHOD

(76) Inventor: Bruce D. Smith, 13018 Woller Creek, San Antonio, TX (US) 78249

( * ) Notice: Subject to any disclaimer, the term of this patent is extended or adjusted under 35 U.S.C. 154(b) by 1 day.

(21) Appl. No.: 11/685,573

(22) Filed: Mar. 13, 2007

(65) Prior Publication Data
US 2008/0224061 A1    Sep. 18, 2008

Related U.S. Application Data

(60) Provisional application No. 60/894,478, filed on Mar. 13, 2007.

(51) Int. Cl.
*G01J 1/00* (2006.01)
*G01T 1/00* (2006.01)
(52) U.S. Cl. .............. 250/370.09; 250/394; 378/17; 378/70
(58) Field of Classification Search .............. None
See application file for complete search history.

(56) References Cited

U.S. PATENT DOCUMENTS

| | | | |
|---|---|---|---|
| 4,833,327 A | | 5/1989 | Hart |
| 4,857,737 A | | 8/1989 | Kamae et al. |
| 5,128,864 A | * | 7/1992 | Waggener et al. ............. 378/14 |
| 5,175,434 A | | 12/1992 | Engdahl |
| 5,567,944 A | | 10/1996 | Rohe et al. |
| 5,665,971 A | | 9/1997 | Chen et al. |
| 5,696,806 A | * | 12/1997 | Grodzins et al. ............. 378/86 |
| 5,742,056 A | | 4/1998 | Valentino et al. |
| 5,841,141 A | | 11/1998 | Gullberg et al. |
| 5,861,627 A | | 1/1999 | Basko et al. |
| 5,930,384 A | | 7/1999 | Guillemaud et al. |
| 6,292,525 B1 | | 9/2001 | Tam |
| 6,330,298 B1 | | 12/2001 | Tam |
| 6,539,103 B1 | | 3/2003 | Panin et al. |
| 6,628,984 B2 | | 9/2003 | Weinberg |
| 6,665,369 B2 | | 12/2003 | Ukita |
| 6,791,090 B2 | | 9/2004 | Lin et al. |
| 7,015,477 B2 | | 3/2006 | Gunter |
| 7,183,554 B2 | * | 2/2007 | Gallagher et al. ......... 250/358.1 |

(Continued)

OTHER PUBLICATIONS

Smith, B.D. (Mar. 2005), "Reconstruction methods and completeness conditions for two Compton data models," J. Opt. Soc. Am. A., vol. 22(3), pp. 445-459.

(Continued)

*Primary Examiner*—David P Porta
*Assistant Examiner*—Yara B Green
(74) *Attorney, Agent, or Firm*—Eric W. Cernyar, P.C.

(57) ABSTRACT

An approach for the selection of Compton camera shapes, configurations, positions, orientations, trajectory paths, and detector element sets is provided for collecting data for analysis using the surface integral and integral-of-line-integral methods of reconstruction Compton data. Methods are introduced for (1) selecting one or more imaging lines through a radioactive distribution for which approximations of integrals of radioactivity are to be derived, (2) selecting and using Compton camera relative positions, relative orientations, and detector element sets that "correspond to" the selected imaging lines to collect the needed data; and (3) deriving approximations of integrals of radioactivity along those imaging lines. This methodological approach is used to reconstruct line integrals, cross-sections, local volumes, parallel projections, and cone-beam projections of radioactive distributions.

53 Claims, 14 Drawing Sheets

U.S. PATENT DOCUMENTS

| | | | |
|---|---|---|---|
| 7,359,480 B2 * | 4/2008 | Slaughter et al. | 378/57 |
| 2003/0197128 A1 * | 10/2003 | Tumer | 250/370.09 |
| 2004/0021083 A1 | 2/2004 | Nelson | |
| 2004/0065838 A1 * | 4/2004 | Tumer | 250/370.09 |
| 2004/0116797 A1 * | 6/2004 | Takahashi et al. | 600/407 |
| 2004/0251419 A1 | 12/2004 | Nelson et al. | |
| 2005/0211909 A1 | 9/2005 | Smith | |
| 2006/0163485 A1 * | 7/2006 | Stearns et al. | 250/363.03 |

OTHER PUBLICATIONS

Lucas C. Parra (Aug. 2000). "Reconstruction of cone-bam projections from Compton scattered data." IEEE Transactions on Nuclear Science vol. 47, No. 4, pp. 1543-1550.

Basko et al., "Application of spherical harmonies to image reconstruction for the Compton camera," Phys Med. Biol., 43:887-894, 1998.

Cree and Bones, "Towards direct reconstruction from a gamma camera based on Compton scattering," 13 (2):398-407, 1994.

Evans et al., "Deconvolution of shift-variant broadening for Compton scatter imaging," Nuclear Instruments and Method in Physics Research A, 422:661-666, 1999.

Smith, "Cone-beam tomography: recent advances and tutorial review," Optical Engineering, 29(5):524-534, 1990.

Smith, "Image reconstruction from cone-beam projections: necessary and sufficient conditions and reconstruction methods," IEEE Transactions on Medical Imaging, MI-4:14-28, 1985.

Brunetti, Golosio and Cesareo, "A correction procedure for the self-absorption artifacts in x-ray Compton tomography", X-Ray Spectrom. 2002; 31:377-382.

Hirasawa and Tomitani, "An analytical image reconstruction algorithm to compensate for scattering angle broadening in Compton cameras," 2003 Publishing Ltd. (UK), stacks.iop.org/PMB/48/1009.

Tomitani and Hirasawa, "Image reconstruction from limited angle Compton camera data," Phys. Med. Biol. 47 (2002) 2129-2145.

* cited by examiner

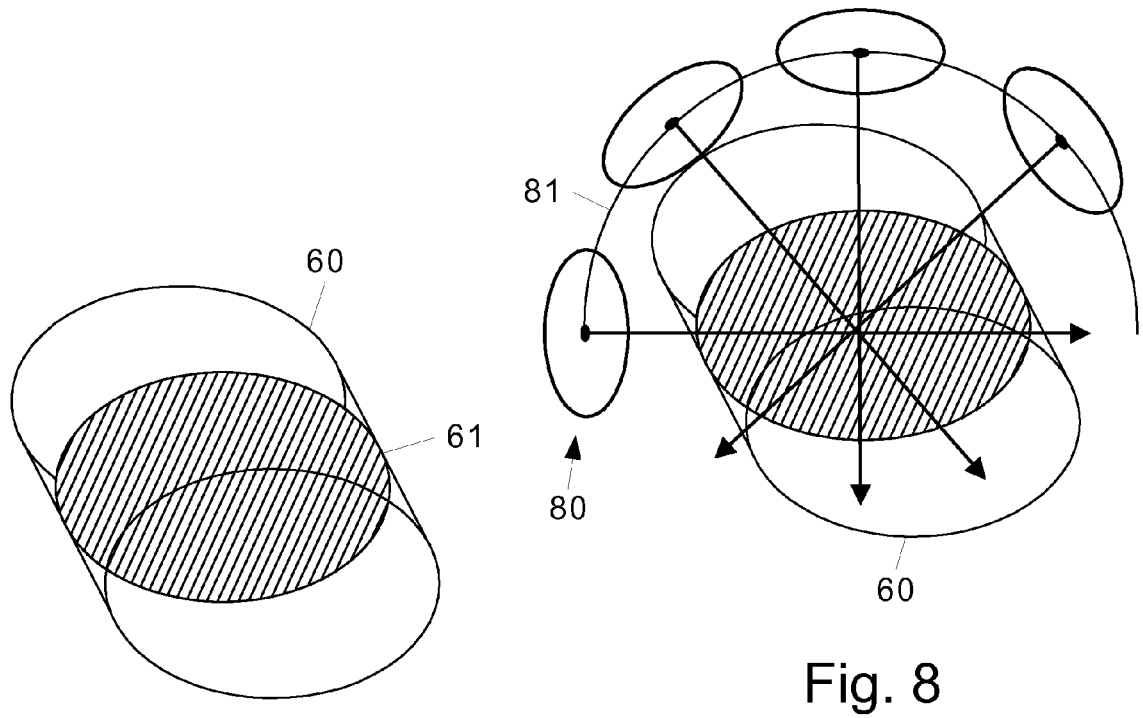
Fig. 6
Fig. 8
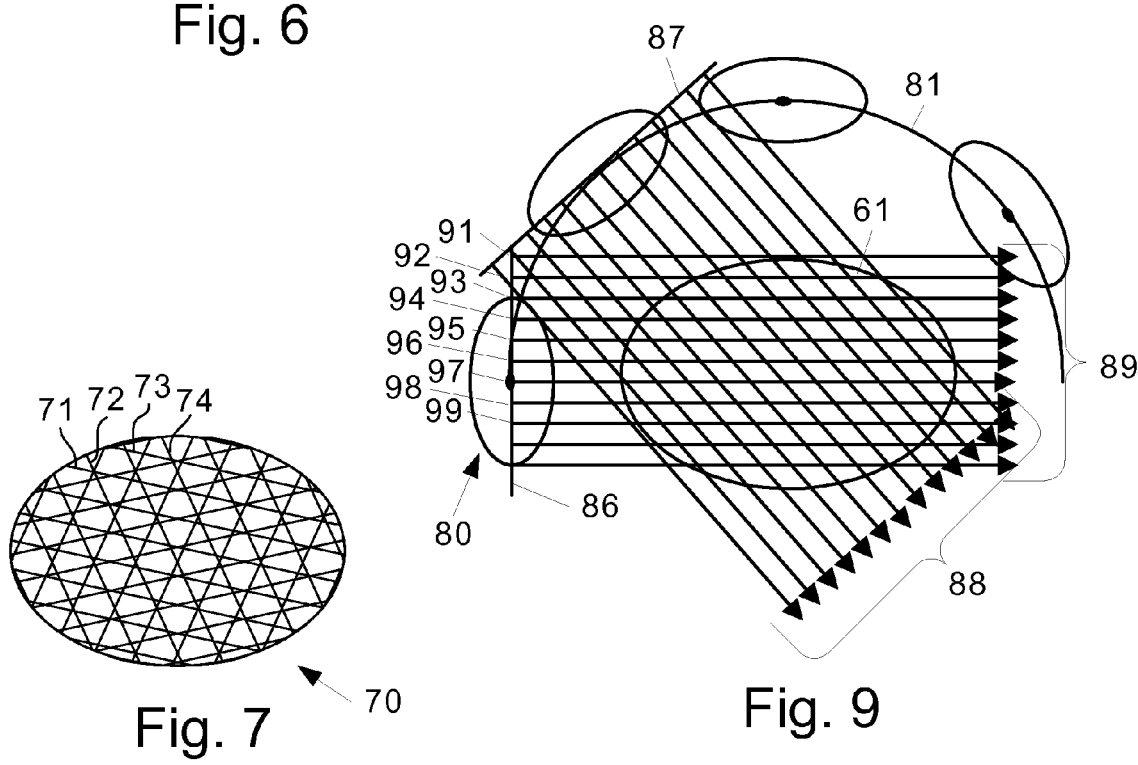
Fig. 7
Fig. 9

COMPTON CAMERA CONFIGURATION AND IMAGING METHOD

RELATED APPLICATIONS

This application claims the benefit of, and hereby incorporates by reference, my U.S. provisional patent application no. 60/894,478, entitled "Paradigms for Designing Compton Cameras and Telescopes and Reconstruction Methods for Redundant Data Sets," and filed on Mar. 13, 2007.

FIELD OF THE INVENTION

This invention relates generally to imaging methods using a Compton camera, and more particularly to the selection of Compton camera shapes, configurations, positions, orientations, trajectory paths, and detector element sets to collect data for analysis using the imaging methods.

BACKGROUND OF THE INVENTION

Compton's Scattering Law

In 1923, Arthur Holly Compton observed that X-ray and gamma ray photons frequently scatter and lose energy (and gain wavelength) when they interact with electrons in matter. This phenomenon—which demonstrates that light has particle, as well as wave properties—has come to be known as Compton scattering. Observations have shown that this phenomenon can be characterized by the following Compton scattering equation (also known as Compton's law):

$$\lambda' - \lambda = \frac{h}{m_e c}(1 - \cos\psi)$$

where $\lambda$ and $\lambda'$ are the wavelengths, respectively, of the photon before and after the scattering; h is Planck's constant, $m_e$ is the mass of the electron, c is the speed of light, and $\psi$ is the angle by which the photon's heading changes, also known at the Compton scatter angle.

Compton Camera Principles

It is possible to create a device, known as a Compton camera, with a first detector and a second detector, each of which contains one or more detector elements, to cause and record incidents of Compton scattering, and from the detected information reconstruct a radioactive distribution from which the detected gamma and x-ray photons originated. In a Compton camera, the first detector, sometimes referred to as a scatter detector, has one or more first detector elements operable to scatter a photon interacting with a first detector element and to approximately measure an amount of energy lost by said photon as a result of said interaction. The second detector, in some Compton camera embodiments referred to as an absorption detector (although a Compton camera need not have second detector elements that fully absorb the detected photons), has multiple second detector elements operable to detect the scattered photon.

A Compton camera is typically associated with an instrument that is operable to record incidents in which a photon interacts with first and second detector elements, and in a manner that preserves information about the identities or positions of the first and second detector elements with which the photon interacted, and that also preserves information approximately indicating an amount of energy lost by the photon when it interacted with the first detector element. This can be done by partitioning the measured incidents into measurement bins. Typically, for each pair of first and second detector elements, Ne corresponding measurement bins are provided, each of which represents different detected energy levels. Each measurement bin could be tagged with three variables j, l, and k representing photons counted in the kth energy bin that interacted with the jth first element and the lth second element.

Because it is known that the energy of a photon is defined by the following equation:

$$E = \frac{hc}{\lambda}$$

if one knows the initial wavelength $\lambda$ of the detected gamma or x-ray photon (which can be known by knowing the radioactive isotope producing the radiation), then one can compute the post-scatter wavelength $\lambda'$ of the photon from the measured energy loss. From this information, one can deduce the approximate angle of the scatter in accordance with the Compton scattering equation. Thus, assuming that the initial wavelength $\lambda$ of the detected gamma or x-ray photon is known, then each measurement bin would represent a count of detected photons with an approximate corresponding scatter angle $\psi$.

The inventor's article *Reconstruction methods and completeness conditions for two Compton data models* in the March 2005 edition of the Journal of the Optical Society of America, discusses the limitations of three prior art reconstruction methods and suggests two new reconstruction methods for Compton data. That article did not, however, set forth a methodological approach to selecting Compton camera shapes, configurations, positions, orientations, trajectory paths, and detector element sets to collect data for analysis using the two new reconstruction methods. Indeed, page 455 of the article stated that "[i]t is not immediately obvious what shapes, configurations, and motions of the detectors will satisfy [the] completeness conditions" described in that paper. The article also suggested that not until "an advantageous shape, configuration and motion of the detectors has been selected," would it "be wise to build a full-scale Compton imaging system."

Traditional paradigms for designing Compton cameras have been based on prior art reconstruction methods. But those paradigms are not optimal if the two Compton data models described in the 2005 paper are used to reconstruct.

SUMMARY OF THE INVENTION

The present invention is directed to an approach for the selection of Compton camera shapes, configurations, positions, orientations, trajectory paths, and detector element sets to collect data for analysis using the "surface integral" or "integral of cone-beam line integral" Compton data reconstruction methods. The present invention introduces the concepts of (1) selecting one or more imaging lines through a radioactive distribution for which approximations of integrals of radioactivity are to be derived, (2) selecting and using Compton camera relative positions, relative orientations, and detector element sets that "correspond to" the selected imaging lines to collect the needed data; and (3) deriving approximations of integrals of radioactivity along those imaging lines. The present invention applies this approach to reconstructing line integrals, cross-sections, local volumes, parallel projections, and cone-beam projections of radioactive distributions. The present invention also extends this approach to exploiting redundant measurement bins and redundant Compton data sets; developing a "Lampshade" detector (described further herein); performing "variable virtual collimation"; and using management measurement bin data sets for reconstruction. The present invention also develops applications for medical imaging, far field imaging such as celestial tomography, and inspections of containers for contraband materials.

BRIEF DESCRIPTION OF THE DRAWINGS

FIG. 6 illustrates a selected cross-section of a radioactive distribution.

FIG. 7 illustrates a plurality of selected imaging lines that are widely and numerously distributed throughout a coplanar cross-section.

FIG. 8 illustrates the movement of the simple "circle-dot" Compton camera along a semi-circular trajectory around a radioactive distribution.

FIG. 9 illustrates moving this Compton camera through multiple points lying on a plurality of tangential segments to a semicircular trajectory around the radioactive distribution.

DETAILED DESCRIPTION

Finding the Conical Surface Region From Which a Detected Photon Originated

Figure 1:
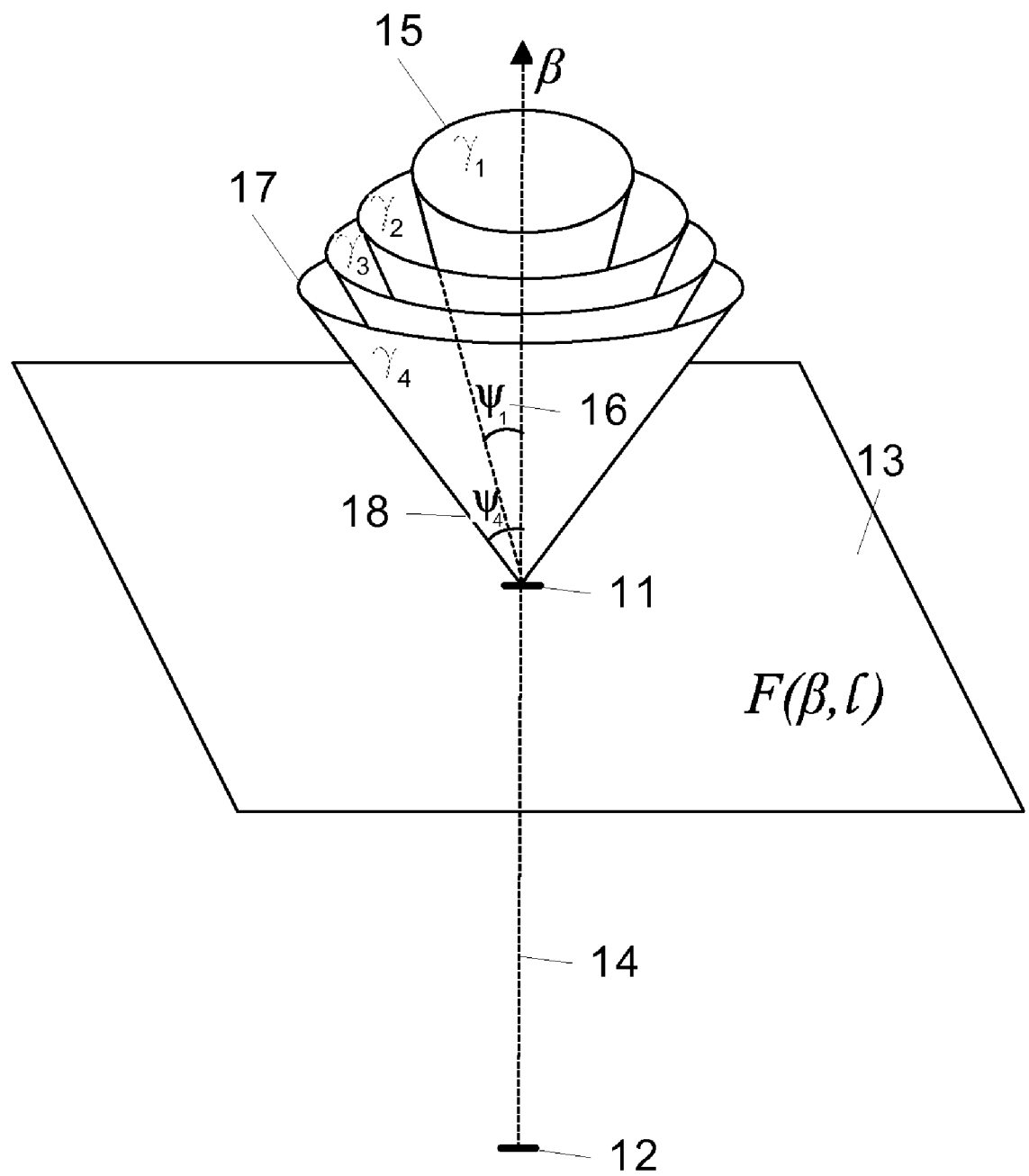
FIG. 1 illustrates how, from a pair of first and second detector elements in a Compton camera, an intermediate function F can be known for a plane intersecting the first detector element and perpendicular to the line connecting the first and second detector elements.

FIG. 1 illustrates how for a pair of first and second detector elements 11 and 12 in a Compton camera, there is a cone of origin associated with each photon that is counted, the cone having an apex at the first detector element 11, an axis of symmetry 14 collinear with the line connecting the first and second detector elements 11 and 12, and a conical angle 16, 18, etc., that corresponds to the difference between the pre- and post-scatter wavelengths of the photon.

If it is known that a photon has interacted with a first detector element 11, and is scattered (deflected) by the first detector element 11 toward a second detector element 12, then it is known that the photon originated from a point that lies on the surface of a cone whose apex is at the first detector element 11 and whose axis of symmetry 14 is the line containing first and second detector elements 11 and 12. If the pre- and post-scatter wavelengths $\lambda$ and $\lambda'$ of the photon can be deduced from the detected data, then it can be determined that the photon originated from a cone having a Compton scatter angle $\psi$ between the axis of symmetry 14 and the cone itself.

FIG. 1 illustrates several different concentric cones including concentric cones 15 and 17. Cone 15 represents a conical region of origin of a photon $\gamma_1$, detected by first and second detector elements 11 and 12, that was scattered at angle $\psi_1$ 16 when it interacted with first detector element 11. Cone 17 represents a conical region of origin of a detected photon $\psi_4$ that was scattered at angle $\psi_4$ 18 when it interacted with first detector element 11.

Deriving the Intermediate Function S or $S_{CB}$ From Measurement Bin Data

Assume that there are $N_e$ measurement bins (not shown) corresponding to the first and second detector elements 11 and 12, where $N_e$ represents the number of energy bins used to preserve information approximately indicating an amount of energy lost by the photon when it interacted with the first detector element. If these measurement bins have collected a statistically significant amount of data, then—if one ignores distortions associated with the Doppler effect and the Klien-Nishina distribution of scatter angles—each measurement bin roughly approximates the integral of the radioactivity over the corresponding cone.

In sections 3 and 4 of the inventor's article *Reconstruction methods and completeness conditions for two Compton data models* in the March 2005 edition of the Journal of the Optical Society of America, which is herein incorporated by reference, the inventor describes reconstruction steps to derive an intermediate function S or $S_{CB}$ from the measurement bin data in a manner that compensates for Doppler effect blurring and the Klein-Nishina distribution of scatter angles. The intermediate function $S(\Phi,\beta,\psi)$ represents the surface integral of a distribution of radioactivity emanating from a cone whose apex is $\Phi$, axis of symmetry is $\beta$, and half-angle is $\psi$. The intermediate function $S_{CB}(\Phi,\beta,\psi)$ represents the integral of cone beam line integrals of a distribution of radioactivity emanating from a cone whose apex is $\Phi$, axis of symmetry is $\beta$, and half-angle is $\psi$. An improvement on step 1 of the inventor's March 2005 paper is set forth in section 5.5.2 of my provisional application.

Deriving the Intermediate Function F From S or $S_{CB}$

In sections 3 and 4 of the inventor's March 2005 paper, the inventor describes an intermediate function $F(\beta,l)$ that can be derived from the intermediate functions S or $S_{CB}$. Using the cone-beam-line-integrals model for Compton data, the relationship between F and $S_{CB}$ is characterized by the following formula:

$$F(\beta, \Phi \cdot \beta) = \lim_{\varepsilon \to 0} \int_0^\Pi S_{CB}(\Phi, \beta, \Psi) H_\varepsilon(\cos\Psi) \sin\Psi d\Psi$$

where $$H_\varepsilon(t) = \begin{cases} 1/\varepsilon^2 & \text{for } |t| < \varepsilon \\ -1/t^2 & \text{for } |t| \geq \varepsilon \end{cases}$$

Using the surface integral model for Compton data, the relationship between F and S is characterized using the following two formulas, which use another intermediate function F:

$$C(\beta, \Phi \cdot \beta) = -\lim_{\varepsilon \to 0} \int_0^\Pi S_{CB}(\Phi, \beta, \Psi) p_\varepsilon(\cos\Psi) d\Psi$$

$$F(\beta, l) = \frac{1}{\Pi} \frac{\partial}{\partial l} C(\beta, l)$$

where $$p_\varepsilon(t) \triangleq \begin{cases} 1/t & \text{for } |t| < \varepsilon \\ 0 & \text{otherwise} \end{cases}$$

If all the surface integrals or all the integrals of cone beam line integrals are known for every cone emanating from a common apex and sharing a common axis of symmetry, then the intermediate function F is known for the plane intersecting that apex and perpendicular to that axis of symmetry. Stated more abstractly, if the function $F(\beta,l)$ is known at $(\beta_1,l_1)$, then it can be said that F is known on the plane whose normal is the unit vector $\beta_1$ and is at a distance $l_1$ from the origin as measured along its normal.

FIG. 1 also graphically illustrates how one can go from measuring photons interacting with elements 11 and 12 from all possible scatter angles $\psi$ to knowing F for the plane 13 intersecting element 11 and perpendicular to the axis of symmetry 14 defined by elements 11 and 12. In short, if there are a sufficient number of measurement bins associated with detector elements 11 and 12 and a sufficient amount of data is collected by those bins to approximate an integral over all possible scatter angles $\psi$ (which can range from about 0 to about 180 degrees) then one can compute an approximate value of F for the detector element pair (11, 12).

Deriving the Integral of Radioactivity on a Line From Sufficient Calculated Values of F One can relate the integral of radioactivity along the straight line that intersects the point $\underset{\to}{x} \in \mathfrak{R}^3$ and is collinear with the unit vector $\underset{\to}{\varphi}$ to a set of intermediate functions F for planes that intersect a given line using the following equation:

$$P(\underset{\to}{x}, \underset{\to}{\varphi}) = \frac{1}{2\pi} \int_0^\pi F\left(\underset{\to}{\beta_{\theta,\varphi}}, \underset{\to}{x} \cdot \underset{\to}{\beta_{\theta,\varphi}}\right) d\theta$$

where $$P(\underset{\to}{x}, \underset{\to}{\varphi}) = \int_{-\infty}^\infty f(\underset{\to}{x} + s\underset{\to}{\varphi}) ds,$$

$$\underset{\to}{\beta_{\theta,\varphi}} = (\cos\varphi\sin\theta, \sin\varphi\sin\theta, \cos\theta)^\tau,$$

$$\underset{\to}{\varphi} = (\cos\varphi, \sin\varphi, 0)^\tau,$$

and $$\underset{\to}{\varphi_\perp} = (\sin\varphi, -\cos\varphi, 0)^\tau.$$

It should be noted that the value the $\underset{\to}{x} \cdot \underset{\to}{\beta_{\theta,\varphi}}$ is the distance of a plane from the origin. This distance is measured along the plane's perpendicular, which is the unit vector $\underset{\to}{\beta_{\theta,\varphi}}$. Furthermore, the plane contains the point $\underset{\to}{x}$. Hence, the foregoing equation integrates all the values of the function F associated with the planes that contain the straight line.

Figure 2:
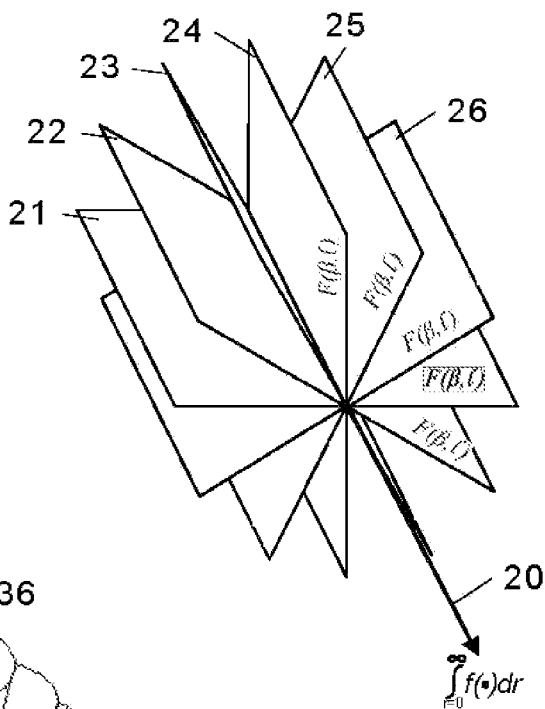
FIG. 2 illustrates what is herein referred to as the "F1 condition," meaning that if the function F is known on sufficiently many and sufficiently widely angularly distributed planes that contain a given "imaging line," then the line integral along the imaging line can be reconstructed.

The foregoing relationship between the line integral and set of F values is much easier to comprehend if given the following geometric interpretation, in conjunction with FIG. 2:

If the function F is known on almost every plane (or on sufficiently many and sufficiently widely angularly distributed planes 21, 22, 23, 24, 25, 26, etc.) that contain a given line 20, then the line integral along this line 20 can be reconstructed from these values of F.

This condition is herein referred to as F1—the line-integral from F condition.

A Simple Compton Camera for Obtaining Line Integral Data

Figure 3:
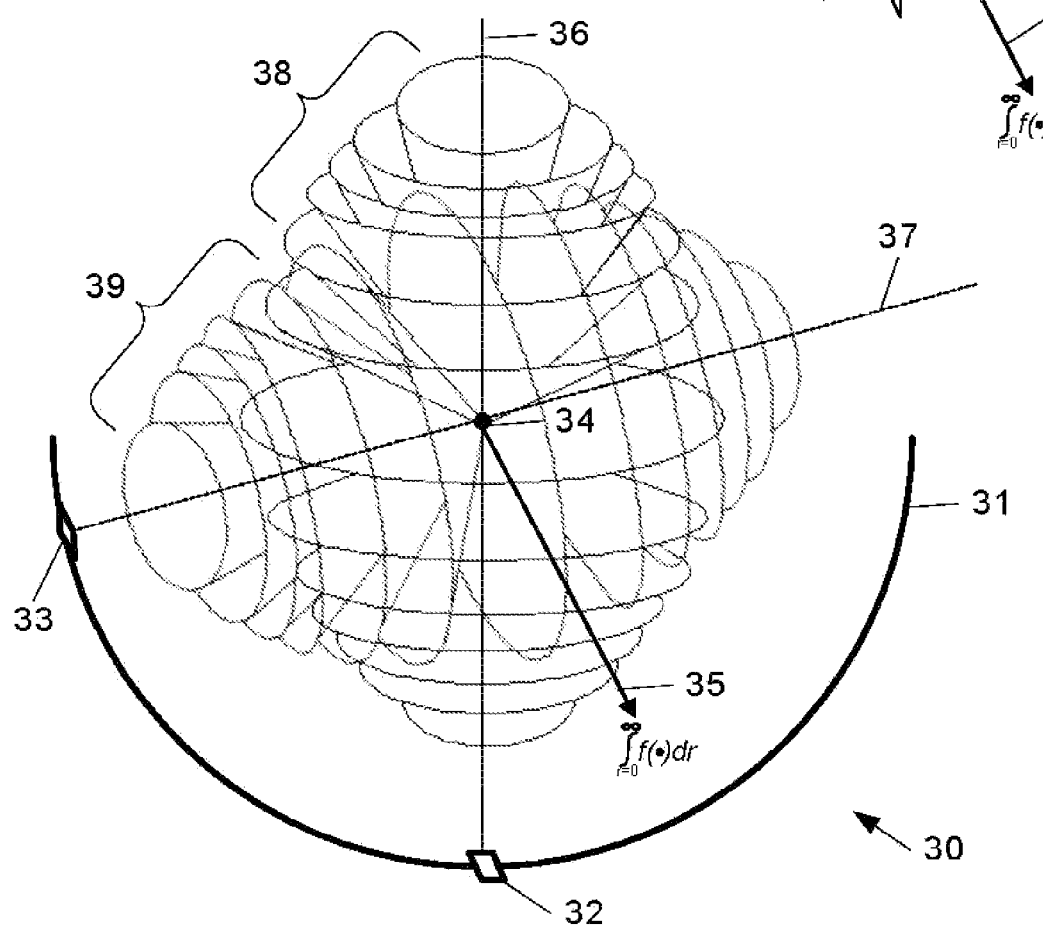
FIG. 3 illustrates a simple Compton camera designed to satisfy the F1 condition.

FIG. 3 illustrates a simple Compton camera 30 designed to satisfy the F1 condition. Compton camera 30 comprises a second detector 31 that consists of multiple detector elements (32, 33, etc.) numerously and evenly (or at least widely) distributed around a half-circle centered on a coplanar single first detector element 34. Here, "half-circle" means a two-dimensional half-circle, not a three-dimensional half-sphere. This simple Compton camera 30 is shaped and configured to obtain an approximation of the integral of the radioactivity along a line —hereinafter referred to as an "imaging line"— that intersects the first detector element 34 and that is perpendicular to the plane in which first and second detector elements lie.

Each pair of first and second detector elements—for example, detector element pair (34, 32) and detector element pair (34, 33)—is associated with multiple measurement bins corresponding to different detected energy levels and/or scatter angles. (The stacked concentric cones 38 and 39 centered on lines 36 and 37, respectively, in FIG. 3 represent different conical regions, defined by various detected photon scatter angles, from which a given detected photon may have originated).

If the measurement bins associated with a detector element pair collect statistically significant data, one can approximately compute the value of the intermediate function F for the plane intersecting the first detector element of the detector element pair and perpendicular to the line connecting the elements of each detector element pair. For example, the measurement bins associated with detector element pair (34, 33) would provide data enabling a computation of F for a plane perpendicular to the line 37 connecting detector elements 33 and 34. Likewise, the measurement bins associated with detector element pair (34, 32) would provide data enabling a computation of F for a plane perpendicular to the line 36 connecting detector elements 32 and 34.

Importantly, one may observe that the planes perpendicular to lines 36 and 37 intersect at line 35. Indeed, all of the planes perpendicular to the lines connecting any first, second detector element pair on this simple Compton camera 30 would intersect along line 35, much like the planes 21-26 in FIG. 2 intersect along line 20. Because the second detector elements are widely and numerously distributed 180 degrees around the coplanar first detector element, F can be computed for a numerous collection of angularly well-distributed planes containing the imaging line 35, thereby satisfying condition F1. Because Compton camera 30 satisfies condition F1, a computer associated with this simple Compton camera 30 can be programmed to determine the integral of radioactivity along the imaging line 35.

Using the ILI and SI Models of Compton Data to Compute a Line Integral

Figure 4:
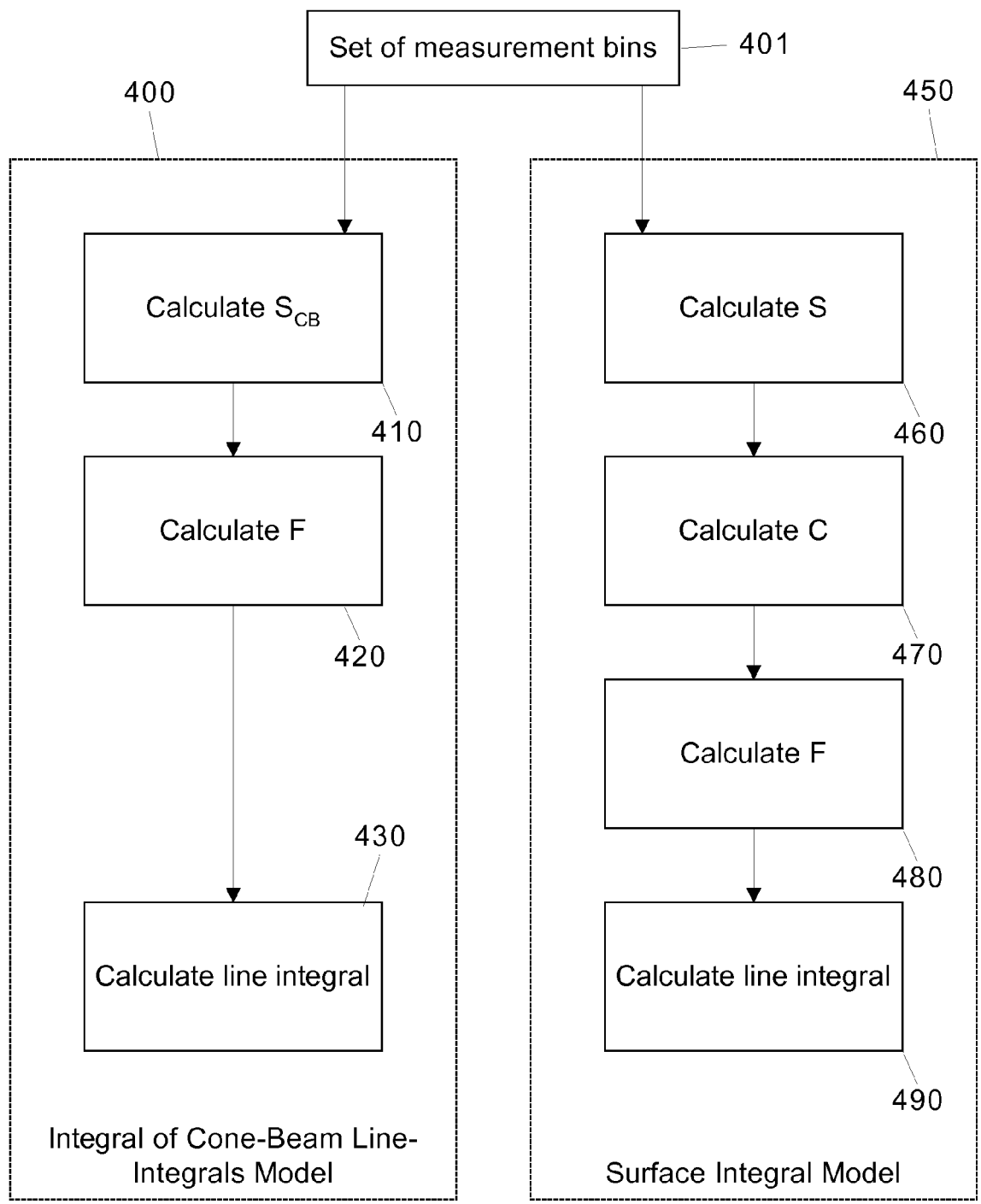
FIG. 4 illustrates two different models of determining an integral of radioactivity along an imaging line.

FIG. 4 illustrates two different models of determining an integral of radioactivity along an imaging line using the measurement bin data 401 associated with a simple Compton camera 30 or a functionally equivalent portion of a more complex Compton camera. In step 410 of the integral of cone-beam line-integrals model ("ILI model") 400, a value for the intermediate function $S_{CB}$ (described above, and further described in my provisional application) is calculated (with numerical approximation) from the measurement bin data 401. In step 420 of the ILI model, a value for the intermediate function F (also described above, and further described in my provisional application) is calculated from the intermediate function $S_{CB}$. In step 430 of the ILI model the line integral of radioactivity is calculated from intermediate function F.

In step 460 of the integral of surface integral model ("SI model") 450, a value for the intermediate function S (described above, and further described in my provisional application) is calculated (with numerical approximation) from the measurement bin data 401. In step 470 of the SI model, a value for the intermediate function C (described above, and further described in my provisional application) is calculated from the intermediate function S. In step 480 of the SI model, a value for the intermediate function F is calculated from the intermediate function C. In step 490 of the SI model, the line integral of radioactivity is calculated from intermediate function F.

If one uses the ILI model of Compton data, one could use the simple Compton camera 30 of FIG. 3 to obtain sufficient measurements to compute an approximation of an integral of the radioactivity along an imaging line using a single camera 30 position and orientation with respect to the radioactive distribution. But if one uses the SI model of Compton data, camera 30 would need to be moved with respect to the radioactive distribution to obtain values in a neighborhood of the imaging line. This is because in the SI model of Compton data, F is calculated as a partial derivative of C. Hence, to obtain a value of F at a point, the values of C in a neighborhood of that point will be needed.

Exploiting Redundant Data

Figure 5:
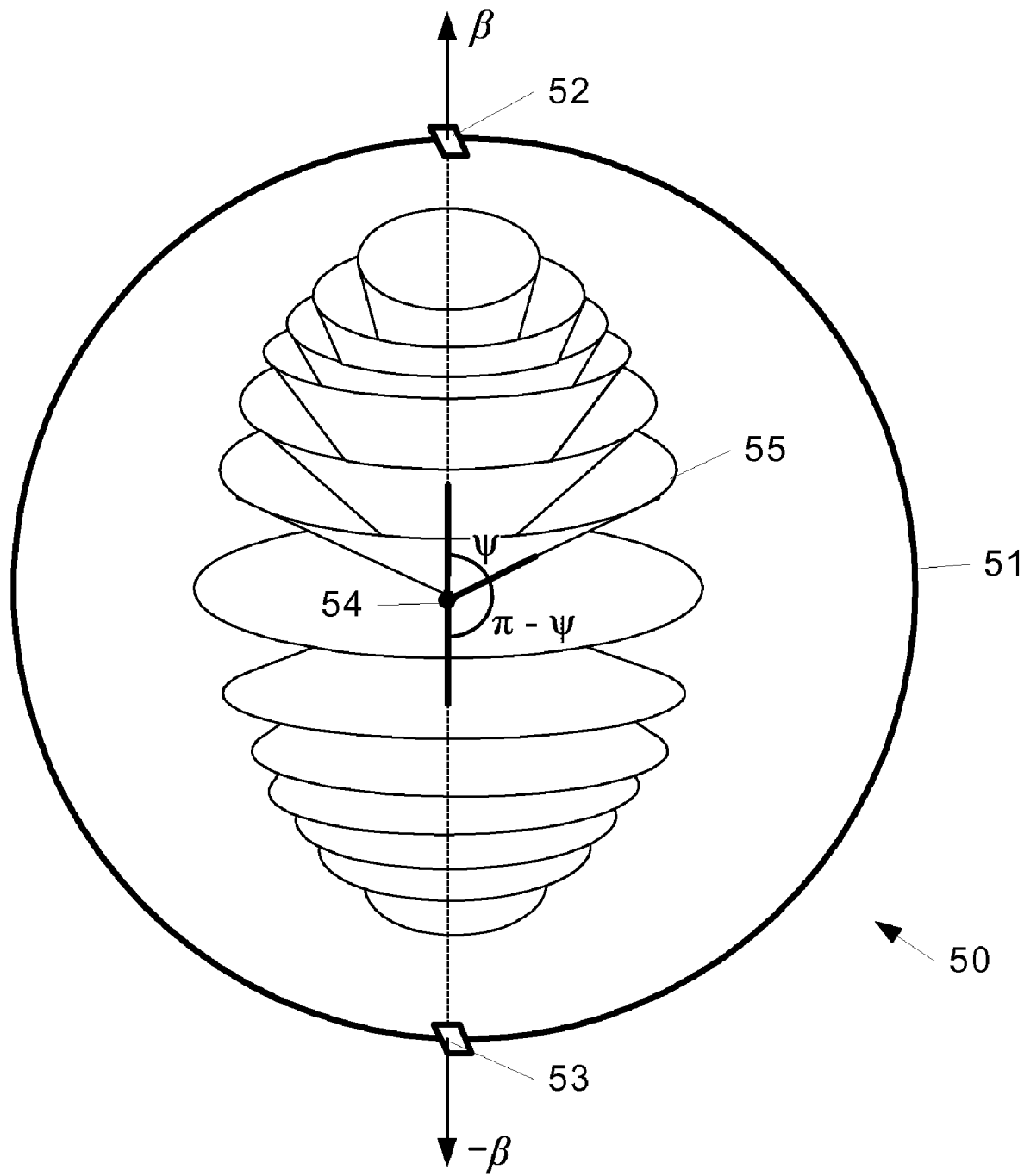
FIG. 5 illustrates a simple "circle-dot" Compton camera designed to collect redundant data for computing the integral of radioactivity along an imaging line.

FIG. 5 illustrates a Compton camera 50 designed to collect redundant data for computing the integral of radioactivity along an imaging line. Compton camera 50 comprises a second detector 51 that consists of multiple detector elements (52, 53, etc.) widely and numerously distributed on opposite sides of a coplanar single first detector element 54. More particularly, the elements of second detector 51 are distributed around a circle centered on detector element 54. Compton cameras of this type will hereinafter be referred to as having a "circle-dot" configuration.

From FIG. 5 it can be seen that the cone 55 associated with the first, second detector element pair (54, 52) and scatter angle ψ will be identical to the cone 55 associated with the first, second detector element pair (54, 53) and scatter angle π-ψ. From this it can be deduced that the data collected by the measurement bin associated with first, second detector element pair (54, 52) and scatter angle ψ will be redundant with the data collected by the measurement bin associated with the first, second detector element pair (54, 53) and scatter angle π-ψ.

This redundancy can be exploited by blending the data (e.g., by using a weighted, angle-dependent aggregation of the data) associated with redundant measurement bins in order to compensate for the Klein-Nishina distribution of scatter angles and to improve accuracy. This is particularly useful to the extent that large angle data is being used to compensate for problematic small angle data, which is distorted by thermo-noise in the detectors.

Using Line Integral Data to Reconstruct a Cross-Section

If the line-integrals along all lines that lie on a plane are known, it is possible to reconstruct each point on the cross-sectional plane. By extension, it can be said that:

If the function F is known on almost every plane that intersects a cross-sectional plane of the distribution of radioactivity, then each point on the cross-sectional plane can be reconstructed.

This condition is herein referred to as F2—cross section from F condition. To reconstruct a cross-section of the distribution of radioactivity from line-integrals along lines that lie on the cross-section, the following notation is used. Let $f(\underline{x})$ for $\underline{x} \in \mathfrak{R}^2$ denote the distribution of radioactivity on the cross-section. The function $p(l, \underline{\theta})$ denote the line-integral of the distribution of radioactivity along the line whose perpendicular makes an angle θ with respect to the horizontal and distance from the origin, as measured along it's perpendicular, is l. This function is mathematically defined as $$p(l, \underline{\theta}) = \int_{-\infty}^{\infty} f(\theta l + \underline{\theta}_T s)\, ds$$

where $$\underline{\theta} = (\cos\theta, \sin\theta)^\tau,$$

-continued and $$\underset{\rightarrow}{\theta} = (\sin\theta, -\cos\theta)^\tau.$$

The two-dimensional Radon inversion formula relates the distribution to the line-integrals as follows:

$$f(\underset{\rightarrow}{x}) = \frac{1}{2\pi^2} \int_{\lim_{\varepsilon \to 0}}^{\pi} \int_{-\infty}^{\infty} H_\varepsilon(\underset{\rightarrow}{x} \cdot \underset{\rightarrow}{\theta} - l) p(l, \underset{\rightarrow}{\theta}) dl d\theta.$$

FIG. 6 illustrates a selected cross-section 61 of a radioactive distribution 60. It will be noted that every plane that intersects the cross-section 61 of the distribution of radioactivity would intersect the cross-section 61 along lines that are coplanar with the cross-section 61.

FIG. 7 illustrates a plurality of selected imaging lines 71, 72, 73, 74, etc., that are widely and numerously distributed throughout a coplanar cross-section 70. Preferably, the lines 71, 72, 73, 74, etc., are distributed in such a manner that cannot be represented as a one-dimensional set of lines. For instance, a one-dimensional set of lines could be a set of lines that intersect each other at a common point, that differ only in their relative angles of intersection, and that can therefore be represented as a one-dimensional function of angular orientation.

FIG. 8 illustrates the movement of the simple "circle-dot" Compton camera 80 along a semi-circular trajectory 81 around the radioactive distribution 60. By taking measurements of the radioactive distribution at each of multiple points along the semi-circular trajectory 81, the Compton camera 80 can be used to approximate integrals of radioactivity along multiple selected imaging lines that are coplanar to, and widely angularly distributed within, the selected cross-section 61. But as suggested above, it is preferable, when reconstructing a cross section of radioactivity, to select imaging lines that are not only angularly well-distributed within the cross-section 61, but also well-distributed with respect to the distance between the imaging line and the center of the selected cross-section 61.

FIG. 9 illustrates moving this Compton camera 80 through multiple points 91-99, etc., lying on a plurality of tangential segments 86, 87, etc., to a semicircular trajectory 81 around the radioactive distribution. Preferably, each tangential segment 86, 87, etc., is long enough to span a projection of the selected cross-sectional portion 61 onto the tangential segment 86, 87, etc. At each of said multiple points 91-99, etc., on each of said tangential segments 86, 87, etc., the Compton camera 80 is used to collect data for sets of parallel imaging lines 88, 89, etc., that intersect the selected cross-section 61 of the distribution 60. By the time the Compton camera 80 has made a complete traverse through the semicircular trajectory 81, data will have been obtained for a multitude of imaging lines 88, 89, etc., that are widely and numerously distributed throughout the selected cross-section 61. It will be noted that equivalent data can be obtained by moving the Compton camera 80 back and forth, incrementally, through the multiple points 91-99, etc., of a single tangent line 90, while incrementally rotating the radioactive distribution 60.

Applying the ILI model to the Compton data, one can then reconstruct a two-dimensional representation of the selected cross section 61 of the radioactive distribution 60. If one wishes to apply, instead, the SI model of Compton data, the Compton camera 80 should be additionally moved in the direction of the axis of the radioactive distribution, on either side of the selected cross section 61, and obtain sufficient measurements in the neighborhood of the cross-section to enable an approximation of the partial derivative of the intermediate function C. One suitable way to obtain these additional measurements would be to rasterize the Compton camera 80, for each tangential segment 86, 87, etc., through a narrow rectangle parallel to the face of the Compton camera 80 and encompassing the corresponding tangential segments 86, 87, etc.

Figures 10, 11, 12:
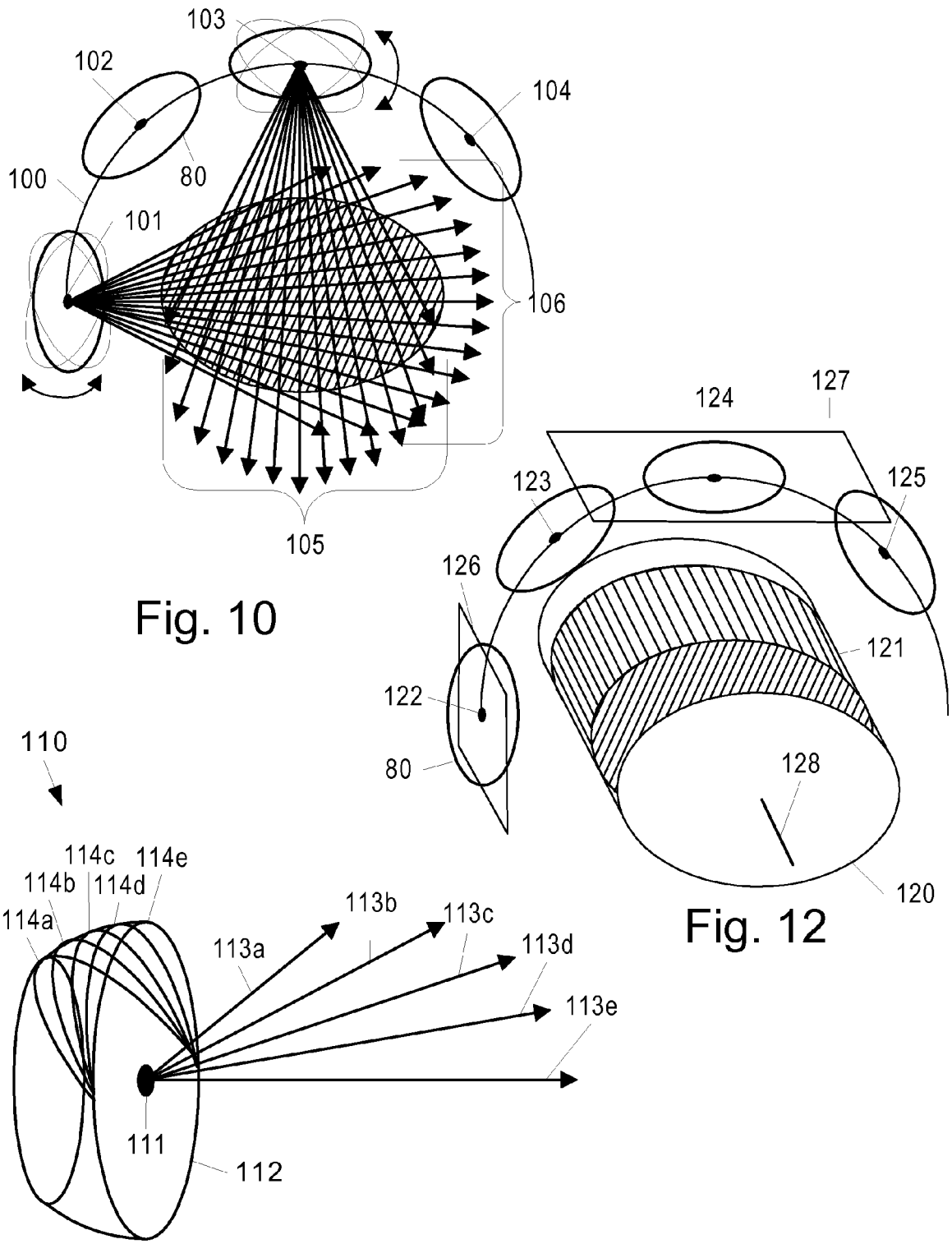
FIG. 10 illustrates an alternative movement trajectory for the Compton camera that involves tilting the Compton camera at multiple points along the semicircular trajectory.
FIG. 11 illustrates a more sophisticated Compton camera which can reconstruct integrals along a set of fan-like imaging lines without tilting the camera.
FIG. 12 illustrates the motion of a simple circle-dot Compton camera to reconstruct a selected volumetric portion within a radioactive distribution.

FIG. 10 illustrates an alternative movement trajectory for the Compton camera 80. The camera 80 is incrementally advanced through multiple points 101, 102, 103, 104 etc., along at least about a 180 degree arc 100 around the radioactive distribution. At each point 101-104, etc., along the trajectory, the camera 80 is incrementally tilted through multiple angular orientations with respect to how directly the face of (i.e., the plane tangent to) the camera 80 is oriented toward the distribution 60. At each of said multiple angular orientations at each of said arc traverse points 101-104, etc., the Compton camera is used to collect data for a fan-like collection of imaging lines 105, 106, etc., that fan out across the entire extent of the selected cross-section 61 of the distribution 60. In this manner also, the Compton camera 80 can be used to reconstruct a two-dimensional representation of the selected cross section 61 of the radioactive distribution 60. It will be noted that equivalent measurements can be obtained by tilting the Compton camera 80 back and forth, incrementally, through the multiple angles 91-99, etc., at a single point 101, while incrementally rotating the radioactive distribution 60.

FIG. 11 illustrates a more sophisticated Compton camera 110 which can reconstruct integrals along a set of fan-like imaging lines 113a-e without tilting the camera 110. Compton camera 110 comprises a second detector 112 with multiple detector elements widely and numerously distributed about the interior surface of a truncated hemisphere. A single-element first detector 111 is positioned at the center of sphere of which the truncated hemisphere would be a part.

As illustrated in FIG. 11, one can identify (and select) different sets of first and second detector elements that correspond to each of the imaging lines 113a-e. In other words, for each of the imaging lines 113a-e, there exists on a plane, coplanar to first detector element 111, and perpendicular to the imaging line, an identifiable and selectable set of second detector elements widely and numerously distributed around element 111. For example, the set comprising the first detector element 111 and the second detector elements adjacent the semicircular arc 114a of the second detector 112 "corresponds to" the imaging line 113a, because (1) this particular set lies on a plane that is perpendicular to the imaging line 113a and intersects first detector element 111 and (2) the second detector elements are widely and numerously distributed on arc 114a around the first detector element 111. Similarly, imaging lines 113b-e correspond, respectively, to sets of detector elements that include second detector elements lying on semicircular arcs 114b-e.

FIG. 11 illustrates, for simplicity, imaging lines 113a-113e fanning out in a two-dimensional fashion. Because the second detector 112 of camera 110 has a truncated hemispherical shape, imaging lines could be illustrated fanning out from the first detector element 111 in three dimensions, each of which imaging lines having identifiable and selectable corresponding detector element sets.

It should be noted that it is not necessary that the second detector elements be distributed on an arc, or that the first detector element be positioned at the locus of the arc. Rather, it is simply desirable that the second detector elements be numerously and angularly well-distributed across at least about a 180 degree span around the coplanar first detector element. In other words, if segments were drawn between the first detector element and each of the second detector elements of a selected detector element set, the vertex joining at least two of the segments would form an angle of almost 180 degrees, with that almost 180-degree angle being subdivided into small angle segments (e.g., preferably 6 degrees or less) by other segments.

Using Line Integral Data to Reconstruct a Local Volume

If the line-integrals along almost all lines that intersect a reconstruction volume are known, it is possible to reconstruct each point in the reconstruction volume. By extension, it can be said that:

If the function F is known on almost every plane that intersects a reconstruction volume, then each point in the volume can be reconstructed.

This condition is herein referred to as F3—the reconstruction volume from F condition. Note that the phrase "reconstruction volume" could mean the entire distribution or just a cross sectional volume of the distribution.

FIG. 12 illustrates the motion of a simple "circle-dot" Compton camera 80 to reconstruct a selected volumetric portion 121 within a radioactive distribution 120. As with FIGS. 8-10's approach to reconstructing cross-sections, the Compton camera 80 is advanced through multiple arc points 122, 123, 124, 125, etc., along at least a half-circle trajectory 129 around the selected volumetric portion 121. At each said arc point 122, 123, 124, 125, etc., the camera is moved in raster fashion across a rectangular raster-coverage portion 126, 127, etc., of a tangent plane to the arc point 122, 124, etc., each said tangent plane being parallel to a longitudinal axis 128 of the half-circle trajectory 129. For each tangent plane, the corresponding rectangular raster-coverage portion 126, 127, etc., should completely enclose a projection of the selected volumetric portion 121 onto the tangent plane. In this manner, the camera 80 collects data for a plurality of imaging lines that are widely and numerously distributed through and about the vicinity of the selected volumetric portion 121. This motion is also suitable for volumetric reconstructions using either the ILI or the SI model of Compton data.

It should be noted that a selected volumetric portion can be approximately reconstructed with imaging lines that lie on a set of parallel cross-sections of the selected volumetric portion. In other words, all of the imaging lines selected to reconstruct the selected volumetric portion 121 may be oriented at a common angle with respect to longitudinal axis 128. Put another way, where the claims provide that imaging lines are to be selected that are widely and numerously distributed through and about the vicinity of a selected volumetric portion 128, it is not necessary that the selected imaging lines be angularly distributed with respect to the longitudinal axis 128.

Developing a Lampshade Detector

Figure 13:
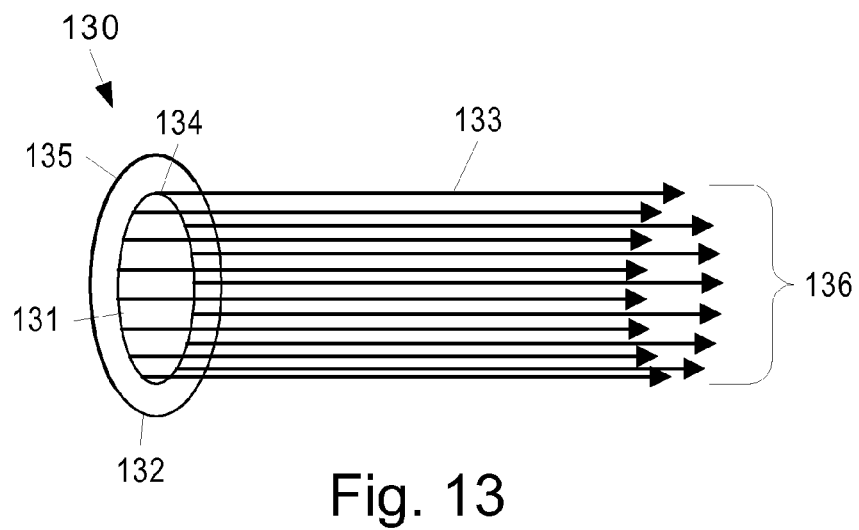
FIG. 13 illustrates a Compton camera consisting of a circular first detector and a concentric circular second detector, each of which includes multiple detector elements widely and numerously distributed about a circle.

FIG. 13 illustrates a Compton camera 130 consisting of a circular first detector 131 and a concentric circular second detector 132, each of which includes multiple detector elements widely and numerously distributed about a circle. Such a camera 130 is capable of simultaneously accumulating data for multiple imaging lines 136 projecting out perpendicularly from the face of the Compton camera 130 and lying on a hollow cylinder that intersects and which is perpendicular to the circular first detector 131. With this Compton camera 130, the set of detector elements corresponding to any given imaging line 133 will consist of some selected group 135 of second detector elements numerously and angularly well-distributed around a coplanar first detector element 134. Indeed, because there are multiple groups of second detector elements that are numerously and angularly well-distributed around a coplanar first detector element 134, there are multiple detector element sets that correspond to any given imaging line 133.

Figure 14:
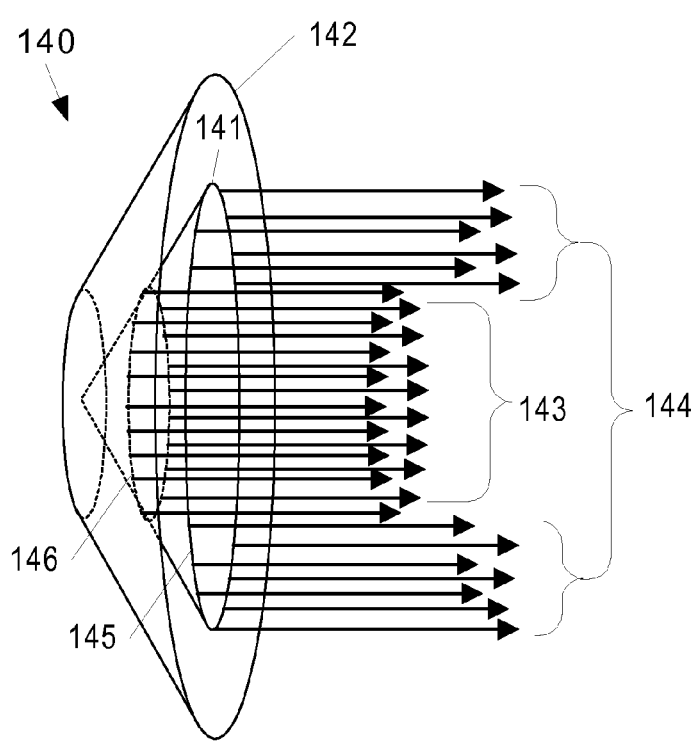
FIG. 14 illustrates a "Lampshade camera" consisting of conically-shaped first and second detectors.

FIG. 14 illustrates a Compton camera, hereinafter referred to as a "Lampshade camera" 140, consisting of conically-shaped first and second detectors 141 and 142, respectively. The first detector 141 has multiple first detector elements distributed in three dimensions across a first cone-shaped surface. Likewise, the second detector 142 has multiple second detector elements distributed in three dimensions across a second cone-shaped surface, and more preferably, across a truncated portion of the second cone-shaped surface. The first and second detectors 141 and 142 are concentric and share a common axis of symmetry. Furthermore, for every detector element on the second detector 142, there is at least one coplanar detector element on the first detector 141 lying on a plane perpendicular to the common axis of symmetry.

Seen another way, the Lampshade camera 140 is a stacked combination of multiple parallel-placed Compton cameras 130, wherein each Compton camera 130 is slightly larger in diameter than the Compton camera 130 to its left (or right), and wherein each Compton camera 130 can accumulate data for a corresponding cylindrical section of imaging lines 143, 144, etc. Accordingly, the Lampshade camera 140 is capable of simultaneously accumulating data for multiple imaging lines 143, 144, etc., parallel to and filling the volume of a cylinder that is perpendicular to the first detector 141 and that intersects the widest cross section 145 of the first detector 141.

Figure 15:
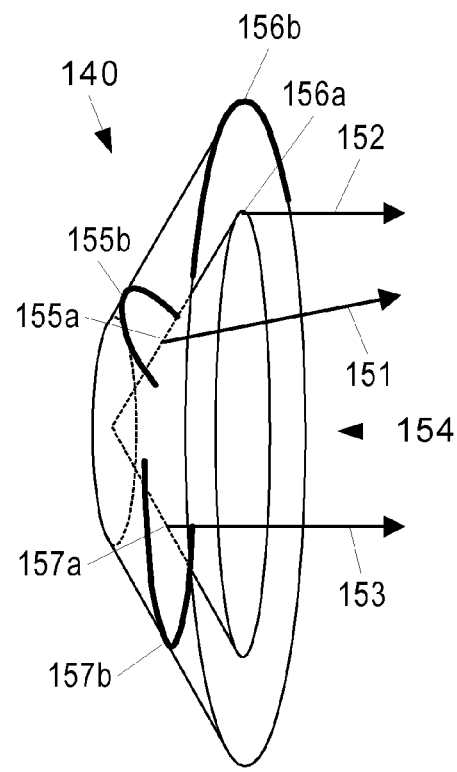
FIG. 15 illustrates the selection of detector element sets on a Lampshade camera that correspond to various imaging lines, some of which are perpendicular and some of which are not perpendicular to the face of the camera.

FIG. 15 illustrates how the three-dimensional distribution of detector elements on the Lampshade camera 140 makes the camera 140 well adapted to take measurements for both imaging lines 152, 153, etc., that are perpendicular to the face 154 of the camera 140, and imaging lines 151 that are not perpendicular to the face 154 of the camera 140. For imaging lines 152 and 153, there are corresponding sets 156b, 157b of second detector elements that are numerously and angularly well-distributed around a coplanar first detector element 156a or 157a. For skewed imaging line 151, there is also a corresponding set 155b (indeed, multiple corresponding sets 155b) of second detector elements that are numerously and angularly well-distributed around a coplanar first detector element 155a.

The foregoing should make it apparent that the amount of relative motion between a Compton camera and a radioactive distribution necessary to perform a cross-sectional or volumetric reconstruction depends, in part, on the shape and configuration of the Compton camera detector elements. For example, fewer movements of a Lampshade camera 140 would be needed to gather data necessary for a cross-section or volumetric reconstruction than would be required using a simple circle-dot Compton camera 80. Simply put, a Lampshade camera 140 at a single orientation and position can measure a much larger fraction of the "numerously and widely distributed" set of imaging lines whose measurements are desired for a cross-sectional or volumetric reconstruction. A Lampshade camera 140 can take also measurements for a large and widely distributed set of imaging lines simultaneously, making it very well adapted for taking measurements needed for a volumetric reconstruction.

Figure 17:
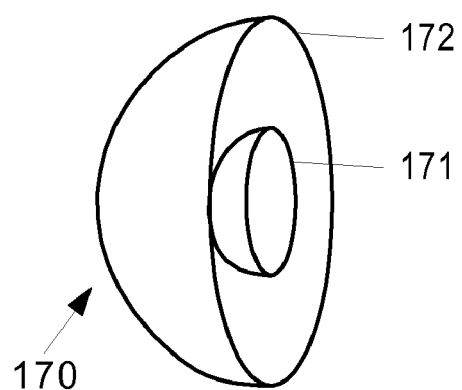
FIG. 17 illustrates an alternative configuration for a Compton camera comprising detectors shaped like nested hemispheres.

FIG. 17 illustrates an alternative configuration for a Compton camera 170. Compton camera 170 comprises a first detector 171 having multiple first detector elements distributed in three dimensions across a first hemispherically-shaped surface, and a second detector 172 having multiple second detector elements distributed in three dimensions across a second hemispherically-shaped surface. The second hemispherically-shaped surface surrounds the first hemispherically-shaped surface.

Figure 16:
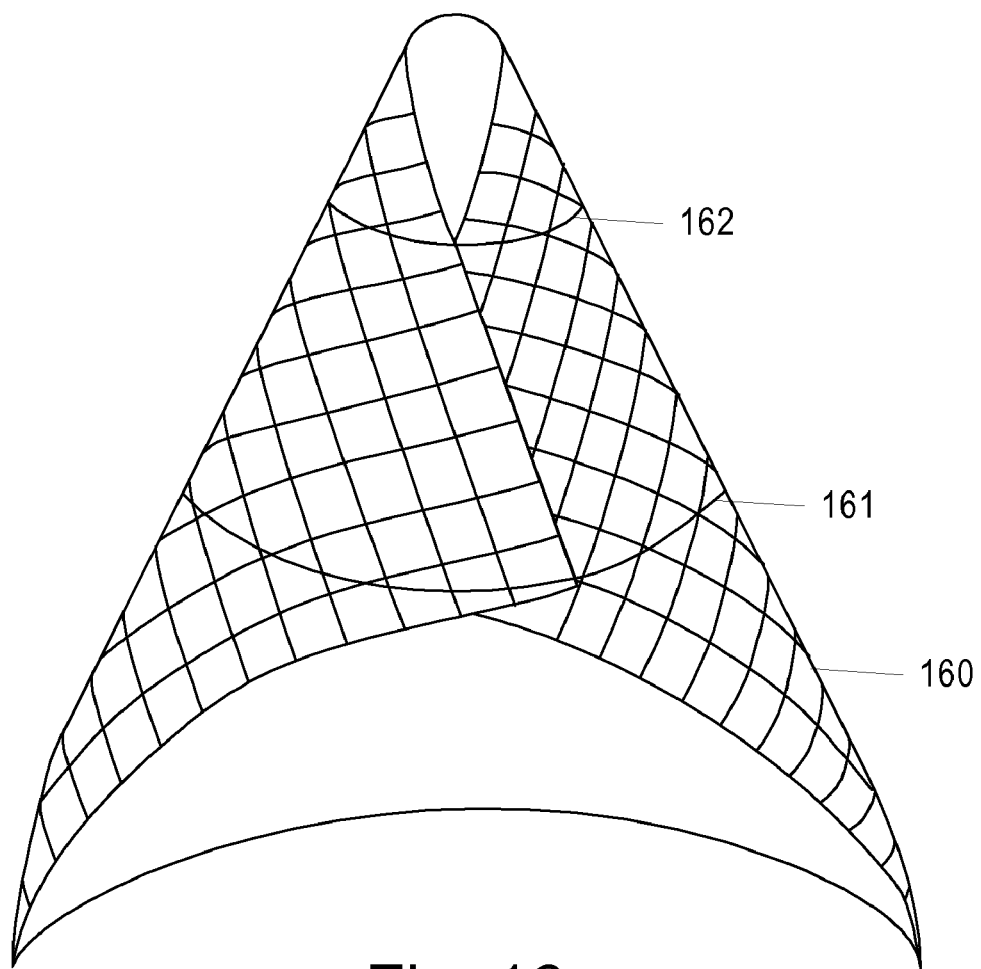
FIG. 16 illustrates a sheet detector twisted, like a piece of engineering graph paper, into the shape of a cone.

However, it is believed that a Lampshade camera 140 may be easier to build than the double-hemisphere detector 170 of FIG. 17. Since a cone is a developable surface, the grids for the detectors could be laid out like a cone that is formed by twisting a piece of engineering graph paper 160, as shown in FIG. 16. Likewise, a Lampshade camera could be fabricated from two sheets of detector elements that are twisted into the shape of a cone, and optionally truncated along lines 161 and 162. Such a Lampshade camera would have first detector elements distributed across the first cone-shaped surface in a manner resembling grids on a piece of engineering graph paper twisted into the shape of a truncated or untruncated cone; and second detector elements distributed across the second cone-shaped surface in a manner resembling grids on a piece of engineering graph paper twisted into the shape of a truncated cone Using Line Integral Data to Reconstruct a Parallel Projection There is a parallel-projection of condition F1, which is:

If the function F is known on almost every plane whose normal is perpendicular to a given direction and intersects the distribution, then the parallel projection in the given direction of the distribution can be reconstructed.

This condition is herein referred to as F4—parallel projection from F condition. Condition F4 makes possible the production of a parallel projection of the distribution of radiation. Producing a parallel projection of a distribution has a directional discriminating capability that is important in certain applications such as the inspection of trucks, ships, etc, for contraband nuclear material. A gross gamma detector such as a Geiger counter will count photons that originated from any direction. Because of this lack of directional discrimination capability, distinguishing between naturally occurring background radioactivity and say shielded radioactive material will be difficult using such devices. In contrast, if F4 is used to produce a parallel projection of the distribution in a given direction, then a value in this two-dimensional projection would be proportional to the number of photons that originate along a line that is collinear with the given direction. This would, in effect, discriminate against the photons that have originated in a different direction.

A Lampshade camera 140 is well adapted for taking measurements for reconstructing a parallel projection of a radioactive distribution. If the active area of the Lampshade camera 140 is larger than the parallel projection to be reconstructed, the Lampshade camera 140 can collect all of the needed data at a single position and orientation. For as illustrated in FIG. 14, the Lampshade camera 140 can simultaneously take measurements corresponding to multiple parallel imaging lines 143, 144, etc., widely and numerously distributed across the two-dimensional active area of the camera 140. If the active area of the Lampshade camera 140 is smaller than the parallel projection to be reconstructed, or if a simpler circle-dot Compton camera 80 is used, the measurements needed for a parallel projection can be obtained by moving the camera in a raster fashion across a rectangular raster-coverage portion that completely encloses the parallel projection.

Use of a Lampshade Camera to Inspect Cargo; Variable Virtual Collimation

Figure 18:
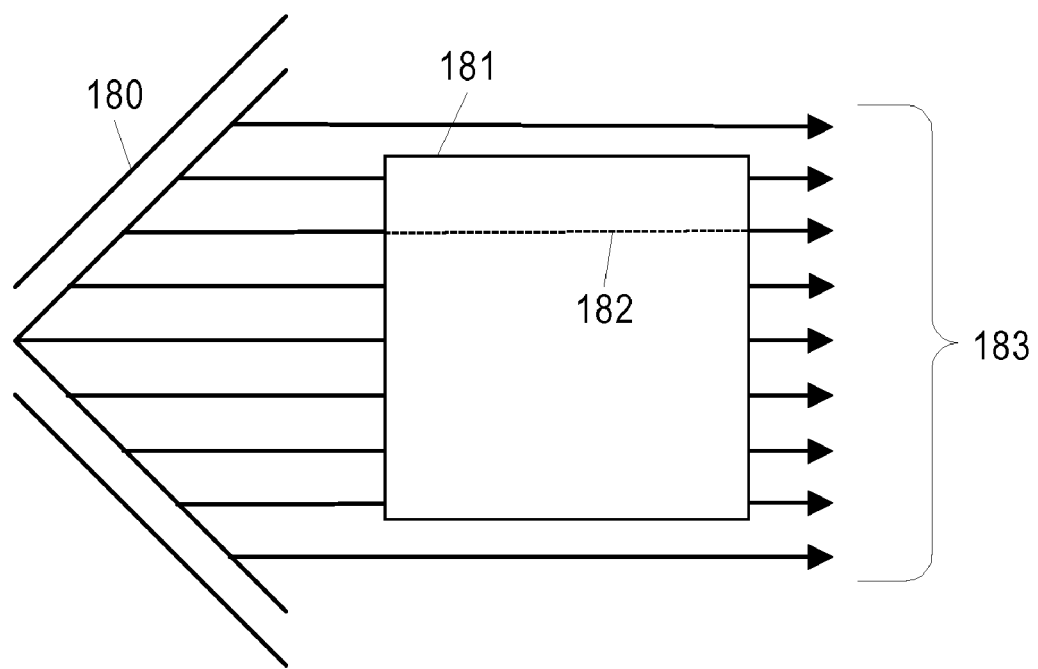
FIG. 18 illustrates a relatively large Lampshade camera used to reconstruct parallel projections of a container.

A Lampshade camera 140 would be useful for inspecting containers, such as cargo containers or suitcases, for nuclear materials. FIG. 18 illustrates a relatively large Lampshade camera 180 used to reconstruct parallel projections of a container 181. A reconstructed parallel projection can be used to isolate, within two dimensions, the location of a radioactive "hot spot" within the container 181. In other words, a parallel projection might indicate that a hot spot is located along the imaging line 182 intersecting the container 181.

Recall it was condition F1 that led to F4. Rather than producing a family of parallel line integrals, condition F1 can be used to produce a family of line-integrals that all converge to a small "focus region," illustrated in FIG. 19. This focus region could be, for example, a point or a segment of a straight line. This would lead to a substantial increase in sensitivity to the radioactivity in the focus region.

Figure 19:
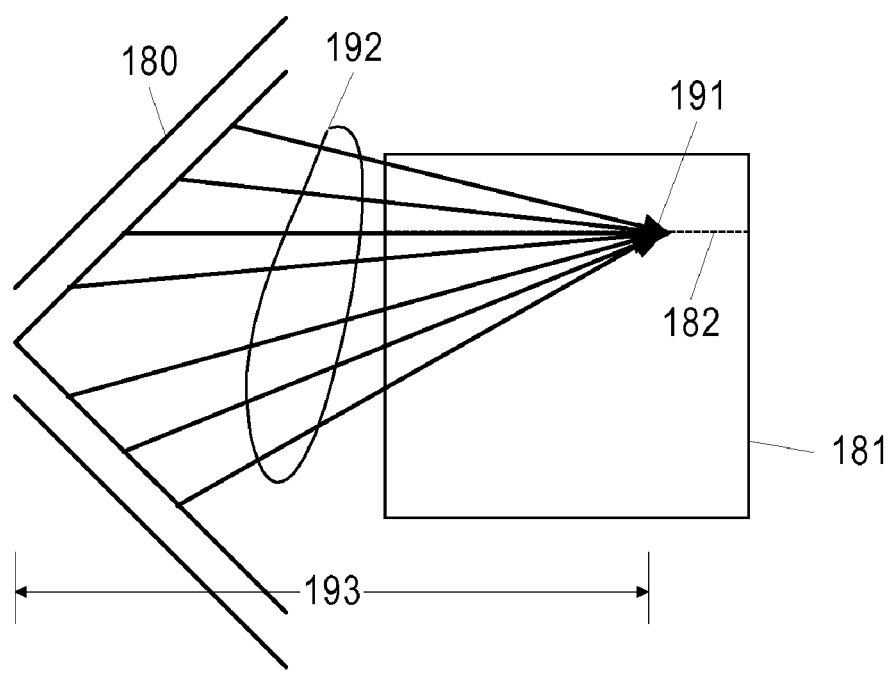
FIG. 19 illustrates using the Lampshade camera to reconstruct a cone beam projection of the container through a selected focal point inside the container.

FIG. 19 illustrates using the Lampshade camera 180 to reconstruct a cone beam projection of the container 181 through a selected focal point 191 inside the container 181. One type of cone beam projection would be an aggregative representation of radioactivity for a plurality of selected imaging lines 192 that converge on a selected focal point 191 in the container 181 or other radioactive distribution. After using a parallel projection to isolate a hot spot, either new measurements can be taken, or measurements already collected by the Lampshade camera 180 can be used, to reconstruct a cone beam projection of the radioactive distribution through a point lying along the imaging line 182. By comparing the cone beam projections for different focal points lying along imaging line 182, one could pinpoint the location of a detected hot spot.

In one embodiment, the Lampshade camera 140 would be versatile enough that both the parallel projection and cone beam projection reconstructions can be performed using a common data superset of previously recorded incidents. If the Lampshade camera 140 is big enough, relative to the container 181, then the common data superset of recorded incidents could be obtained without changing the relative position or relative orientation of the Lampshade camera 140 with respect to the radioactive distribution. Rather, different detector element sets of the Lampshade camera 140 can be selected to collect the data sets for the imaging lines used to perform both the parallel projection and cone beam projection reconstructions. In another embodiment, the Lampshade camera 140 would take two different sets of measurements for the parallel projection and cone beam projection reconstructions.

Note that the "focal length" 193 of the Lampshade camera 180, which is illustrated in FIG. 19, can be varied. Also note that the "focal point" 191 can be adjustable up and down. As stated above, these changes can be made without measuring a second data set. Thus, using F1, virtual collimation with an adjustable focus can be achieved with Compton cameras without the need of obtaining additional data.

Virtual collimation with an adjustable focus length will make possible tomosynthesis (TS) that will require little or no motion of the camera. See [Grant, 1972] for the data collection geometries associated with TS. See [Ruttimann et al., 1984, Ruttimann et al., 1989] for examples of techniques for processing the TS data. By making the focus region mentioned previously to be a segment of a straight line, for example, it is possible to produce a two-dimensional TS reconstructed cross-section through a shipping container. Of course, there are other applications for this other than the inspection of container for contraband material.

Use of a Lampshade Camera in Medicine

A Lampshade camera 140 would also be useful in reconstructing relatively small local volumes, such as the head or heart of a patient, where the "active area" of the Lampshade camera—i.e., the widest cross section 145 of the first detector 141—is wider than the distribution projected in the direction of the camera.

Figure 20:
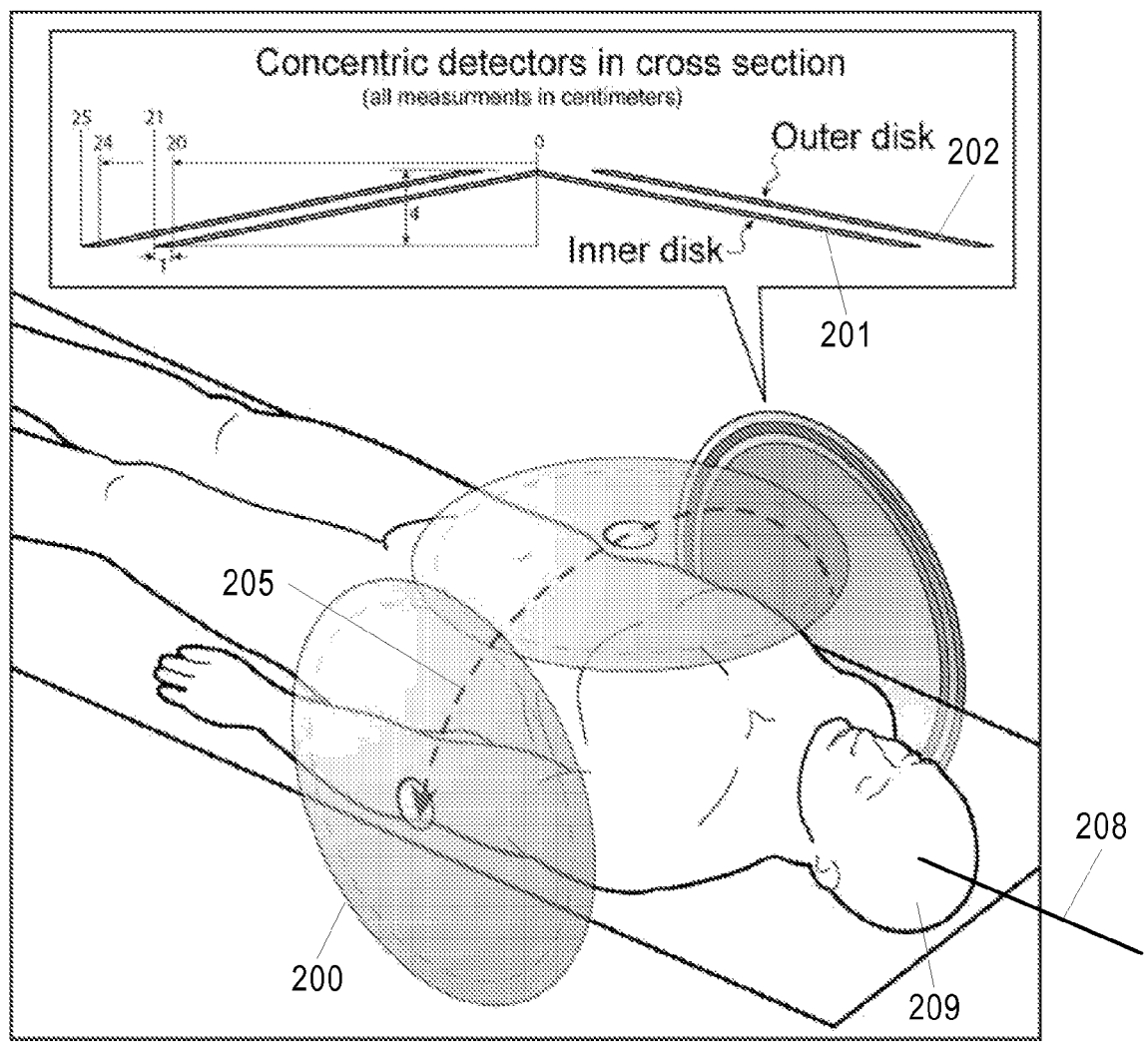
FIG. 20 illustrates a Lampshade camera sized and shaped for imaging a patient.

FIG. 20 illustrates a Lampshade camera 200 sized and shaped for imaging a patient. For example, one embodiment of the Lampshade camera 200 comprises a conically-shaped first detector inner disk 201 having a radius of 20 to 21 centimeters (and corresponding $\pi r^2$ active area) and a depth of 4 centimeters. Lampshade camera 200 further comprises a truncated-cone-shaped second detector outer disk 202 of equal depth and having a maximum radius of 24 to 25 centimeters and a minimum radius of 4 to 5 centimeters. It will be understood that other dimensions may be appropriate.

Lampshade camera 200 can be used for local reconstruction of a selected volume within the patient 209. When taking measurements, the camera face is oriented parallel to a longitudinal axis 208 of the patient 209. The first detector disk 201 spans an area, perpendicular to the detectors' common axis of symmetry, that exceeds the selected volume's width along the patient's longitudinal axis 208. The camera 200 is also moved along at least a half-circle trajectory 205, perpendicular to the patient's longitudinal axis 208, around the patient 209, while maintaining a camera face orientation that is parallel to the patient's longitudinal axis 208 and perpendicular to a plane containing the semi-elliptical trajectory 205. At each of multiple points along the at least a semi-elliptical trajectory, the Lampshade camera 200 collects data sets of incidents of photons emanating from the patient 209. In this manner, Lampshade camera 200 takes measurements along a plurality of imaging lines widely and numerously distributed through a local volume of the patient between two parallel cross-sections spaced about 40 centimeters apart.

From these data sets, it is possible to derive approximations of integrals of radioactivity along imaging lines that are widely and numerously distributed through and about the vicinity of the selected volume. A three-dimensional representation of the radioactivity in the selected volume can then be reconstructed from those multiple integral approximations.

Alternative Trajectories for Reconstructing Volumes

Figure 21:
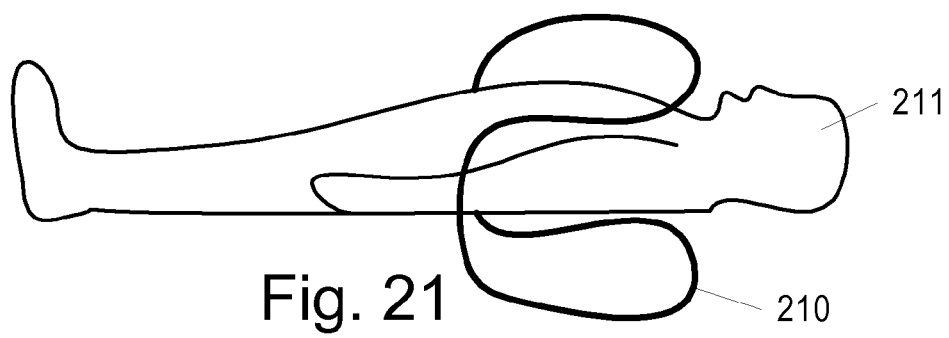
FIG. 21 illustrates a saddle-shaped trajectory around a to-be-reconstructed volumetric portion of a patient.
Figure 22:
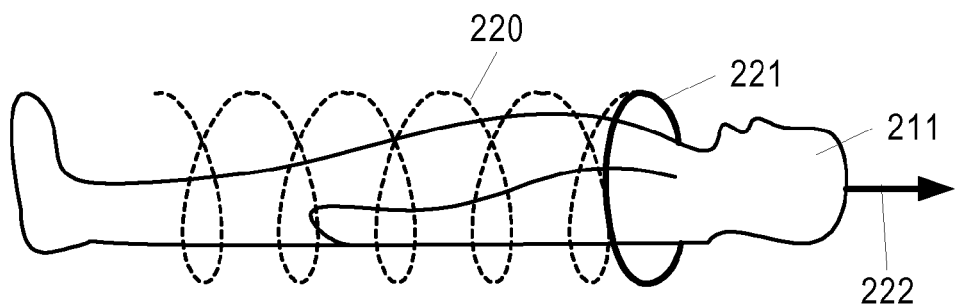
FIG. 22 illustrates a spiral trajectory for a Compton camera around a patient.

In contrast with the semielliptical trajectories previously illustrated for Compton cameras, FIG. 21 illustrates a saddle-shaped trajectory 210 around a volumetric portion of a patient 211 to be reconstructed. FIG. 22 illustrates a spiral trajectory 220 for a Compton camera around the patient 211. This trajectory 220 can be accomplished, among other means, by rotating the Compton camera in a circular trajectory 221 and advancing the radioactive distribution along an axial direction 222.

Compton Camera Instrument

Figure 23:
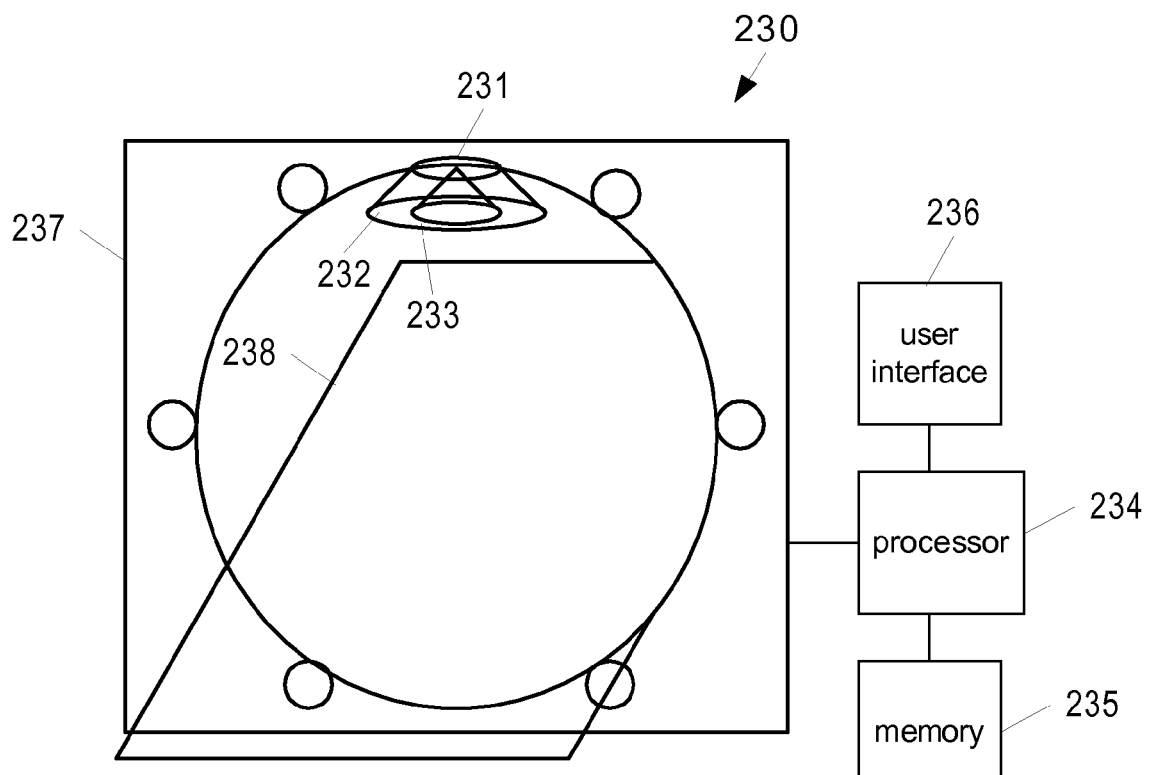
FIG. 23 illustrates a Compton camera instrument, including a Compton camera, a frame for advancing the Compton camera through a trajectory, a processor, memory, and a user interface.

FIG. 23 illustrates a Compton camera instrument 230, including a Compton camera 231 having a first detector 232 and second detector 233, and a frame 237 for advancing the Compton camera 231 and/or patient platform 238 through a relative trajectory. It will be understood, that the first and second detectors can either be physically separate detectors 232 and 233, or may be nothing more than logical subsets of a single common physical detector, wherein the first of two detector elements that interact with a photon is logically defined, for that photon interaction incident, to be a first detector element, and the second element to interact with the photon is logically defined to be a second detector element.

The Compton camera instrument 230 includes a computer processor 234 and memory 235 to enable the instrument 230 to record scattering incidents in a manner that preserves information about the identities or positions of the first and second detector elements with which the photon interacted, while also preserving information approximately indicating an amount of energy lost by the photon when it interacted with the first detector element. The computer processor 234 would also include programs for deriving from collected data sets approximations of integrals of radioactivity along imaging lines and reconstructing from said multiple integral approximations representations of the radioactivity along or in the selected imaging line, cross-section, volumetric portion, parallel projection, or cone-beam projection.

A user interface 236 is provided to enable user selection of an imaging line, cross section, volume, parallel projection, or cone beam projection to be reconstructed. The user interface 236 may also enable user selection of the quality and resolution of the reconstruction, which will be affected by the number of energy bins, detector elements, and imaging lines used to collect data for a reconstruction. There will likely be an inverse relationship between the quality and resolution of a reconstruction and the number of imaging lines selected for a given reconstruction. There will also likely be an inverse relationship between the quality and resolution of a reconstruction and the speed with which the data can be collected. It will be understood that the minimally desirable quality and resolution of a reconstruction will vary depending on the application.

It is conceivable that the user interface 236 may also enable user selection of Compton camera relative positions, relative orientations, and detector element sets that corresponds to a given imaging line, but it is preferred that the computer processor 234 be programmed to both select the imaging lines needed to perform a reconstruction of a user-selected cross-section, volume, or parallel projection, and to select optimal Compton camera relative positions, relative orientations, and detector element sets corresponding to those imaging lines.

Using a Manageable Measurement Bin Data Set for Reconstruction.

In an optional embodiment, the Compton camera instrument 230 would only collect data needed for a given reconstruction. In other words, rather than having a set of measurement bins equal to j times k times l, where j represents the total number of first detector elements in the camera, k represents the number of second detector elements in the camera, and l represents the number of energy bins used to approximate the detected energy loss of a detected photon, the instrument 230 can be designed to collect data for a subset of less than j times k times l measurement bins. For example, the instrument can be designed to collect data for an aggregative set of measurement bins equal to the number of measurement bins used to collect data for any selected imaging line, times the number of imaging lines selected to perform the reconstruction. No measurement bins would be allocated for unselected imaging lines. In such an embodiment, far fewer than j times k times l measurement bins may be needed, meaning that a much more manageable data set can be used for reconstruction.

Application to Far Field Imaging

The imaging approach suggested by this patent application can also be applied to far field imaging. For example, the imaging approach suggested by this patent application can be applied to a Compton telescope used to image a celestial source such as a star.

Figure 24:
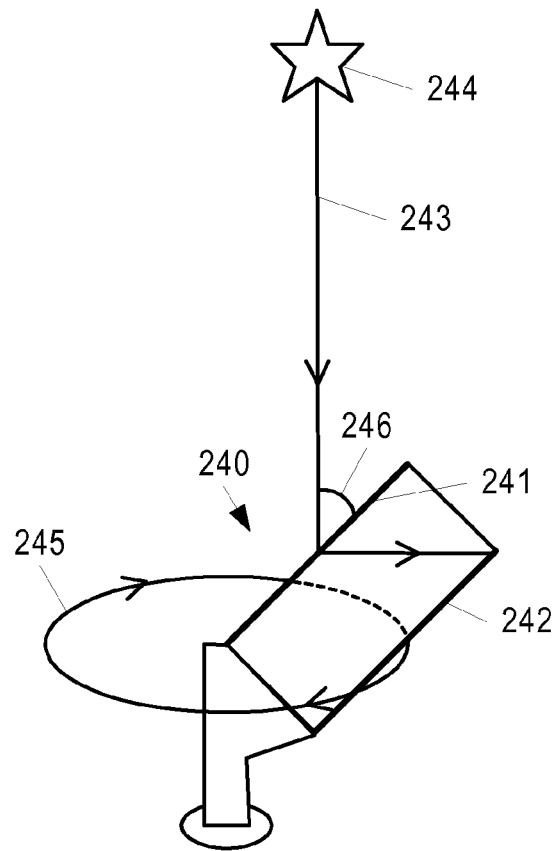
FIG. 24 illustrates an orientation of a conventionally-configured Compton telescope to image a star.

FIG. 24 illustrates an embodiment that applies the imaging approach to a conventionally configured Compton telescope 240, that is, to one in which all the detectors 241, 242 are parallel to themselves and planar. Rather than orienting the face of the detectors so they are perpendicular to the direction 243 of the celestial source 244, the faces would be, say, at an acute angle 246 of between, 10 to 80 degrees, for example, 45 degrees, to the direction 243. This would enhance the measurement of the photons that are scattered perpendicular to the direction 243. To satisfy condition F1, the telescope would be spun around a circular trajectory 245 with the axis of spin being in the direction 243 of the celestial source 244.

This method of imaging a far field source could be expressed as follows:

(a) providing a Compton camera instrument, including a Compton camera having a planar first detector and a planar second detector, the first detector being parallel to the second detector, wherein:

(1) the first detector has a plurality of first detector elements operable to scatter a photon interacting with a first detector element and to approximately measure an amount of energy lost by said photon as a result of said interaction;

(2) the second detector has a plurality of second detector elements operable to detect the scattered photon;

(3) the instrument is operable to record incidents in which a photon interacts with first and second detector elements; and (4) the instrument is operable to record said incidents in a manner that preserves information about the identities or positions of the first and second detector elements with which the photon interacted, and that also preserves information approximately indicating an amount of energy lost by the photon when it interacted with the first detector element;

(b) orienting the Compton camera at a selected acute angle, of between 10 and 80 degrees, to a far field source axis line intersecting the Compton camera and an apparent position of the far field source;

(c) selecting a set of first and second detector elements lying on a common plane perpendicular to the far field axis line;

(d) using said selected detector element set to collect a data of incidents of photons interacting with the elements of the selected detector element set;

(e) rotating the Compton camera through multiple points around the far field axis line while maintaining the previously selected acute angle of the Compton camera to the far field axis line;

(f) at each of said points, repeating steps (c)-(d); and (g) deriving from said data set an approximation of an integral of the radioactivity along the far field axis line.

In addition to imaging celestial sources, this approach could be used to image other "far field" sources such as nuclear power plants.

Figure 25:
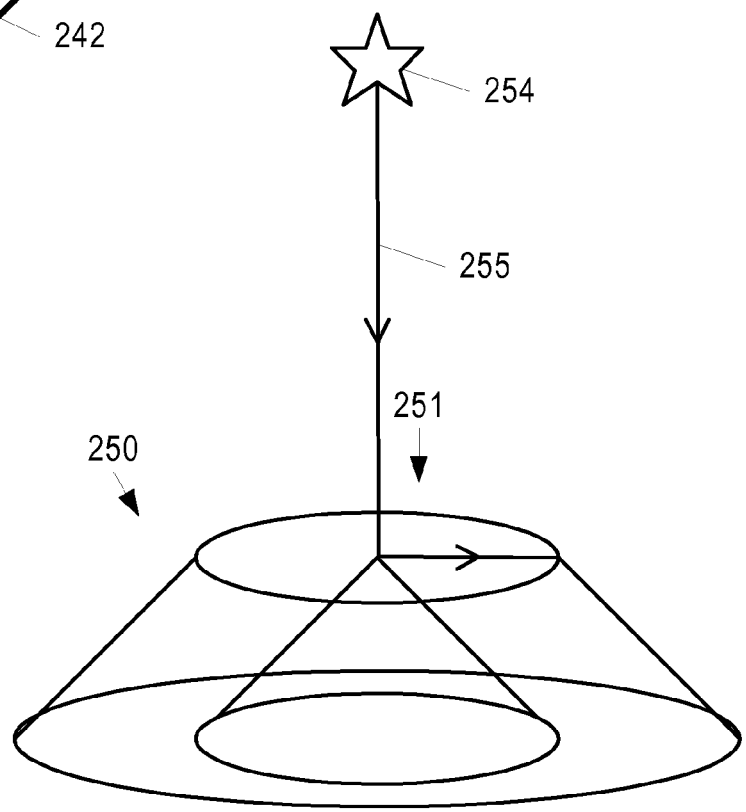
FIG. 25 illustrates the use of a Lampshade camera to image a star.

FIG. 25 illustrates an alternative embodiment would make use of a specially shaped and configured Compton telescope—for example, a Lampshade camera 250—to enhance the detection of "perpendicularly" scattered photons. In this embodiment, the camera face 251 is oriented perpendicular to a celestial source axis line 255 intersecting the Compton camera 250 and an apparent position of the celestial source 254; the celestial source axis line 255 constituting an imaging line along which an approximation of an integral of radioactivity is derived. If one assumes that the celestial source is spherically symmetric, then one can reconstruct a distribution of radiation of the celestial source as a function of the celestial source's radius.

Figure 26:
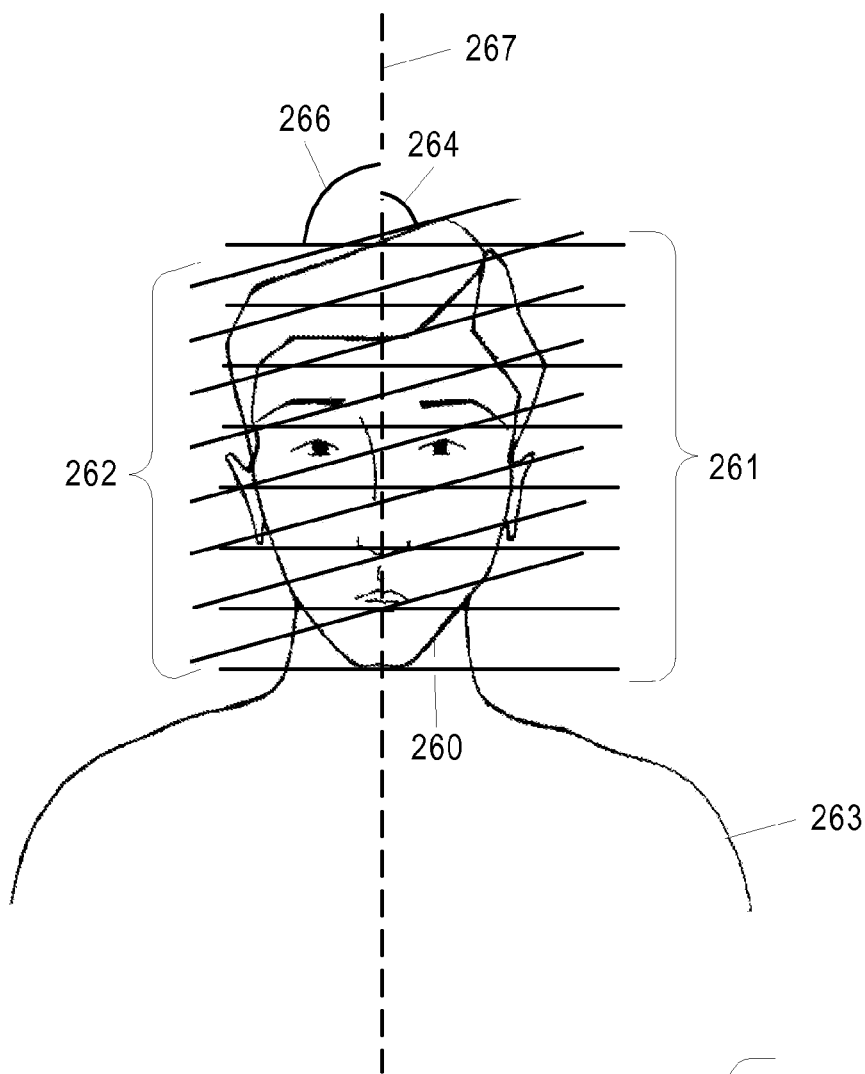
FIG. 26 illustrates sets of imaging lines that pass through a patient's head and neck region without passing through the patient's thorax.
Figure 27:
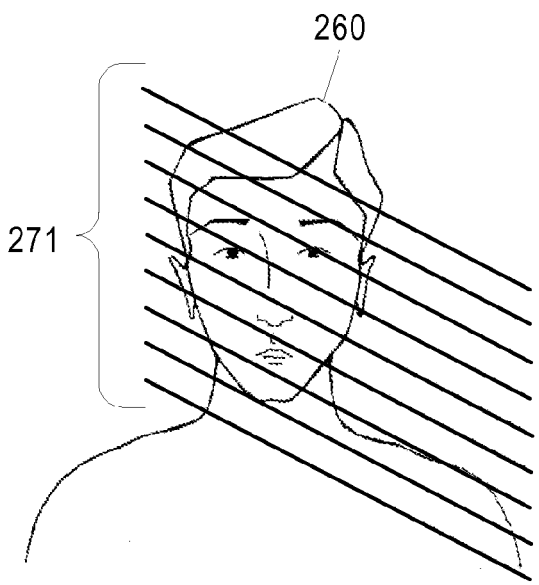
FIG. 27 illustrates a set of imaging lines that pass through not only the patient's head and neck region, but also the shoulders of the patient's thorax.

Calculating Integrals Along More Imaging Lines Than What is Minimally Needed for Reconstruction If one is reconstructing a local portion of a volume—such as a patient's head or midsection—it is preferable that the set of imaging lines that is selected for the reconstruction be imaging lines that pass only through the portion of the volume to be reconstructed. For example, FIG. 26 illustrates sets of imaging lines 261, 262 that pass through a patient's head and neck region 260 without passing through the patient's thorax 263. FIG. 27, by contrast, illustrates a set of imaging lines 271 that pass through not only the patient's head and neck region 260, but also the shoulders of the patient's thorax 263.

The effect of using imaging lines 271 could be mitigated by placing a lead apron around the patient's upper body and a lead collar around the patient's neck. This would largely stop photons originating from the thorax and neck regions. Thus, even if a projection passes through the thorax, few photons from these regions would be counted and as a consequence this projection could be used in the reconstruction process.

It is also possible to improve the quality of a reconstruction by calculating integrals along more imaging lines than what is minimally needed for a reconstruction. A method for doing so is expressed in the following:

(1) selecting a first set of imaging lines 262 that lie on a parallel projection that passes through the selected volumetric portion at a first angle 266 (for example, 90 degrees to the longitudinal axis 267);

(2) selecting a second set of imaging lines 261 that lie on a parallel projection that passes through the selected volumetric portion at a second angle 264;

(3) wherein the first angle 266 is not equal to the second angle 264;

(4) wherein each of the first and second sets of imaging lines 262 and 261 is sufficiently widely and numerously distributed to enable reconstruction of a three-dimensional representation of the selected volumetric portion; and (5) to improve the quality of the reconstructed representation, the reconstruction of the three-dimensional representation of the selected volumetric portion uses multiple integral approximations from both the first and second sets 262 and 261.

Preferably, both the first angle 266 and the second angle 264 are sufficiently large that substantially none of the first or second sets of imaging lines 262 or 261 intersect portions of the distribution outside the section to be locally reconstructed (e.g., a patient's head).

Using Additional Modalities to Detect Contraband and Nuclear Shielding Materials Virtual collimation can be combined with other modalities to increase the likelihood that nuclear contraband will be detected. For example, a device for detecting non-shielded, weakly-shielded, or well-shielded nuclear contraband can be obtained by combining virtual collimation with a neutron source. If the contraband were well-shielded with a heavy metal such as lead, then there would be an increased likelihood that the heavy metal would be detected with the neutron source. On the other hand, if the contraband were not shielded at all, then there would be an increased likelihood that the gamma rays from the nuclear material would be detected with the Compton camera. Alternatively, if the material were weakly shielded, the combination of the probability that the gamma rays would be detected and the probability that the heavy metal would be detected would increase the likelihood that the contraband would be detected.

Pulsed Fast Neutron Analysis (PFNA) has the potential of detecting hidden explosives within cargo containers. An advantageous aspect of neutrons is that they can penetrate deep into a cargo container. In PFNA a beam of neutrons are generated. When the neutrons penetrate into the cargo, the nuclei of the elements that comprise the cargo are excited which causes them to emit a gamma ray that is characteristic of the element. For example a carbon, nitrogen, and oxygen nucleus will emit 4.4 MeV, 5.1 MeV, and 6.1 MeV gamma rays respectively. The measurement of the gamma rays emitted from the nuclei allows one to determine the elements that comprise the cargo. In particular, the amount and ratios of carbon, nitrogen, and oxygen can be determined. Since explosives typically have high nitrogen and oxygen contents, PFNA can be used to discriminate explosive from non-explosive material.

Figure 28:
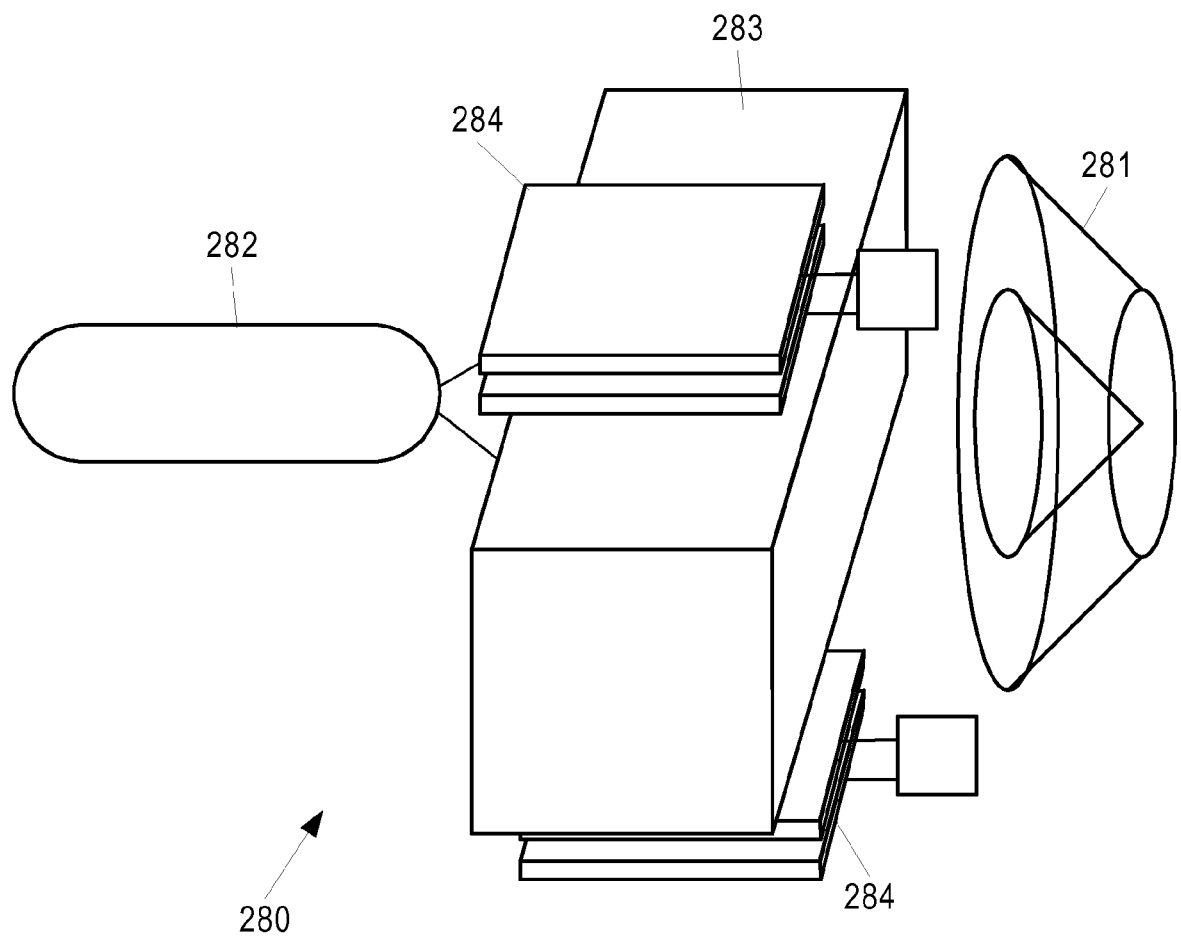
FIG. 28 illustrates a system that combines a Compton camera with either a neutron source to generate neutrons to penetrate a cargo container, and/or a cosmic ray muon imaging device.

FIG. 28 illustrates a system 280 that combines a Compton camera 281 and a neutron source 282 to generate neutrons to penetrate a cargo container 283. The neutrons generated by the neutron source 282 generate the radioactivity that the Compton camera 281 detects.

At the present time the PFNA needs to be within a few feet of the object being inspected. It is extremely desirable to be able to detect hidden explosive at larger distances; for example, 20 to 100 meters. However, the nitrogen and oxygen within the atmosphere makes this difficult. The gamma rays produced by the nitrogen and oxygen within the air can mask the gamma rays being produced within the container. To increase the range of PFNA, an ability to discriminate against the gamma rays produced by the nitrogen and oxygen in the atmosphere is needed.

Variable virtual collimation can be used to discriminate against the undesired gamma rays. The virtual collimation could be used to form a cone beam projection with a focus within the container. This would have the effect of discriminating against the gamma rays that did not originate from within the container.

Of course there are important applications where it is possible to place the object near the neutron source. The inspection of suitcases is an example of this. When this is the case the use of Fast Neutron Analysis (FNA) may be desirable. FNA is the same as PFNA except the collimation that formed the beam of neutrons is not present. This allows the whole object (such as a suitcase) to be interrogated with neutrons simultaneously. If, for example, virtual collimation was used to form a parallel projection, then gamma rays from anywhere within the whole object could be detected simultaneously. Furthermore, the parallel projection would, in effect, discriminate against undesirable background gamma rays. In contrast, if the whole object were to be probed using PFNA, the PFNA beam would have to be raster throughout the whole object. Thus the use of FNA could increase the throughput of the inspection system.

In addition to discriminating against undesired gamma rays, virtual collection can be used to help resolve false alarms. (There are materials other than explosives that have high nitrogen and oxygen contents.) If two Compton cameras with virtual collection capabilities were used with a neutron source, then the position of the material with the high nitrogen and oxygen within the container could be determined.

In addition to Homeland Security, applications of PFNA and FNA include detection of narcotics, landmines, unexploded ordnance and bulk coal analysis.

A combination of virtual collimation with cosmic ray muon imaging device would also be useful for detecting contraband. Indeed, because no harmful rays or particles are used, the system would be so harmless that minimally trained employees or citizens themselves could safely use it.

FIG. 28 illustrates a system 280 that combines a Compton camera 281 capable of performing variable virtual collimation (VVC) with a pair of cosmic ray muon imaging devices 284. Both the Compton camera 281 and the cosmic muon ray imaging (CRMI) devices 284 are passive detection systems that sense two qualitatively different types of phenomenon, not directly perceptible by human senses, regarding the distribution. Such an inspection system 280 would be well adapted for detecting non-shielded, weakly shielded, or well-shielded nuclear contraband. If the contraband were well-shielded with a heavy metal such as lead, then there would be an increased likelihood that the heavy metal would be detected with CRMI. On the other hand, if the contraband were not shielded at all, then there would be an increased likelihood that the gamma rays from the nuclear material would be detected with VVC. The detection of heavy metal or gamma rays would trigger an alarm. Alternatively, if the material were weakly-shielded, the combination of the probability that the gamma rays would be detected and the probability that the heavy metal would be detected would increase the likelihood that an alarm would be issued.

A Methodological, Imaging-Line-Based Approach to Collecting Data for Reconstructing a Line Integral, Cross-Section, Volume, Parallel Projection, or Cone-Beam Projection.

From the foregoing, it can be observed that the respective Compton camera relative positions, orientations, and detector elements sets available or necessary to approximate an integral of radioactivity along imaging lines needed to reconstruct a line, cross-section, volume, parallel projection, or cone-beam projection will depend on the shape and configuration of the Compton camera detector elements. Futhermore, a method of imaging a portion of a radioactive distribution—whether that portion be a line, cross-section, volume, parallel projection, or cone-beam projection of the radioactive distribution—can be initially approached in the following manner:

(1) selecting an imaging line through the radioactive distribution portion for which an approximation of an integral of radioactivity is to be derived;

(2) providing a Compton camera instrument, including a Compton camera having a first detector and a second detector, wherein:

(a) the first detector has one or more first detector elements operable to scatter a photon interacting with a first detector element and to approximately measure an amount of energy lost by said photon as a result of said interaction;

(b) the second detector has multiple second detector elements operable to detect the scattered photon;

(c) the instrument is operable to record incidents in which a photon interacts with first and second detector elements;

(d) the instrument is operable to record said incidents in a manner that preserves information about the identities or positions of the first and second detector elements with which the photon interacted, and that also preserves information approximately indicating an amount of energy lost by the photon when it interacted with the first detector element; and (e) there exists, for at least one given Compton camera position and orientation, a set of first and second detector elements that correspond to the imaging line, meaning that for at least one given Compton camera position and orientation, there exists on a plane perpendicular to the selected imaging line, a set of second detector elements numerously and angularly well-distributed around a coplanar first detector element such that segments connecting the first detector element of the set to at least two of the second detector elements of the set would form an angle of almost 180 degrees;

(3) selecting a Compton camera relative position, relative orientation, and detector element set that corresponds to the imaging line;

(4) implementing said selected Compton camera relative position, relative orientation, and detector element set to collect a data set of incidents of photons emanating from the radioactive distribution and interacting with the elements of the selected detector element set; and (5) deriving from said data set an approximation of an integral of the radioactivity along the imaging line.

It will be understood that the derivation step (5) above may include numerically solving a set of simultaneous equations that relate the integral of radioactivity along the imaging line to the data of the data set.

If the method uses the SI model of Compton data, and only a line integral is being reconstructed, the method can be further developed in the following manner:

(1) selecting a sufficient set of secondary lines parallel to, surrounding, and in the vicinity of the selected imaging line, to enable an approximation of a partial derivative;

(2) for each said secondary line, selecting a Compton camera relative position, relative orientation, and detector element set that corresponds to the secondary line;

(3) for each of said secondary lines, collecting a data set of incidents of photons emanating from the radioactive distribution interacting with the corresponding detector element set; and (4) wherein the deriving step includes applying the surface integral model of Compton data image reconstruction to the collected data sets for both the imaging line and the secondary lines to derive an approximation of a line integral of the radioactivity along the imaging line.

In one embodiment, this method would be carried out utilizing the same Compton camera relative orientation and detector element set corresponding to the imaging line to collect data sets for each of the said secondary lines, while varying only the relative position of the Compton camera in order to collect data sets for each of said secondary lines. Furthermore, the act of varying the relative position of the Compton camera with respect to the radioactive distribution can be accomplished either by (1) moving the camera while keeping the radioactive distribution stationary; (2) keeping the camera stationary while the radioactive distribution is moved; or (3) moving both the camera and the radioactive distribution.

In another embodiment, this method would be carried out by providing a Compton camera instrument that has a sufficient number of first detector elements to enable selection of detector element sets that correspond to each of said secondary lines, without varying the relative position or orientation of the Compton camera with respect to the distribution; and utilizing a plurality of detector element sets to collect data sets for the imaging line and each of said secondary lines simultaneously.

The method of paragraph [0165] can be alternatively described in the following manner:

providing a Compton camera instrument, including a Compton camera having a first detector and a second detector, wherein:

the first detector has one or more first detector elements operable to scatter a photon interacting with a first detector element and to approximately measure an amount of energy lost by said photon as a result of said interaction;

the second detector has multiple second detector elements operable to detect the scattered photon;

the instrument is operable to record incidents in which a photon interacts with first and second detector elements;

the instrument being operable to record said incidents in a manner that preserves information enabling identification of the identities or relative positions of the first and second detector elements with which the photon interacted, and the approximate scatter angle of the photon;

identifying a set of pairs of a selected one of said one or more first detector elements with multiple selected ones of said multiple second detector elements that lie on a common plane, the selected second detector elements being widely distributed with respect to the selected first detector element such that segments connecting at least two of the selected second detector elements would form an angle of almost 180 degrees;

orienting the camera with respect to the radioactive distribution such that a line intersecting the selected first detector element, and perpendicular to the common plane on which the selected first and second detector elements lie, intersects the radioactive distribution;

with the camera at said orientation, collecting a statistically significant data set of incidents of photons emanating from the radioactive distribution interacting with said selected first and second detector elements; and deriving from said statistically significant data sets an approximation of an integral of the radioactivity along an imaging line that intersects the selected first detector element and which is perpendicular to the common plane on which the selected first and second detector elements lie.

When applied to reconstructing a cross-section, the method of paragraph [0165] can be further developed in the following manner:

(1) selecting a cross-sectional portion of the radioactive distribution for reconstruction;

(2) selecting a plurality of imaging lines that lie on a plane containing the selected cross-sectional portion and that are widely and numerously distributed through the selected cross-sectional portion;

(3) for each said selected imaging line:

(a) selecting a Compton camera relative position, relative orientation, and detector element set that corresponds to the imaging line;

(b) implementing said selected Compton camera relative position, relative orientation, and detector element set to collect a data set of incidents of photons emanating from the radioactive distribution and interacting with the elements of the selected detector element set; and (c) deriving from said data set an approximation of an integral of the radioactivity along the imaging line; and (4) reconstructing from said multiple integral approximations a two-dimensional representation of the selected radioactive distribution cross-sectional portion.

When applied to reconstructing a volume, the method of paragraph [0165] can be further developed in the following manner:

(1) selecting a volumetric portion of the radioactive distribution for reconstruction;

(2) selecting a plurality of imaging lines that are widely and numerously distributed through and about the vicinity of the selected volumetric portion;

(3) for each said selected imaging line:

(a) selecting a Compton camera relative position, relative orientation, and detector element set that corresponds to the imaging line;

(b) implementing said selected Compton camera relative position, relative orientation, and detector element set to collect a data set of incidents of photons emanating from the radioactive distribution and interacting with the elements of the selected detector element set; and (c) deriving from said data set an approximation of an integral of the radioactivity along the imaging line; and (4) reconstructing from said multiple integral approximations a three-dimensional representation of the selected volumetric portion.

When applied to reconstructing a parallel projection, the method of paragraph [0165] can be further developed in the following manner:

(1) selecting a plurality of parallel imaging lines from which a parallel projection of the radioactive distribution is to be reconstructed;

(2) for each said selected imaging line:

(a) selecting a Compton camera relative position, relative orientation, and detector element set that corresponds to the imaging line;

(b) implementing said selected Compton camera relative position, relative orientation, and detector element set to collect a data set of incidents of photons emanating from the radioactive distribution and interacting with the elements of the selected detector element set; and (c) deriving from said data set an approximation of an integral of the radioactivity along the imaging line; and (3) reconstructing from said multiple integral approximations a representation of the parallel projection of the radioactive distribution.

When applied to reconstructing a cone beam projection, the method of paragraph [0165] can be further developed in the following manner:

(1) selecting multiple focal points within the radioactive distribution;

(2) for each said focal point, selecting a plurality of converging imaging lines that converge on the focal point;

(a) for each converging imaging line:

(i) selecting a Compton camera relative position, relative orientation, and detector element set that corresponds to the imaging line;

(ii) implementing said selected Compton camera relative position, relative orientation, and detector element set to collect a data set of incidents of photons emanating from the radioactive distribution and interacting with the elements of the selected detector element set; and (iii) deriving from said data set an approximation of an integral of the radioactivity along the imaging line; and (b) for each focal point, reconstructing from said multiple integral approximations an aggregative representation of the radioactivity detected along the corresponding set of converging imaging lines; and (3) comparing the representations of aggregative representations of radioactivity for different focal points to identify points of relatively greater radioactivity.

Before concluding, it is to be understood that the terminology employed in this application is for the purpose of describing particular embodiments. Unless the context clearly demonstrates otherwise, it is not intended to be limiting. In this specification and the appended claims, the singular forms "a" "an" and "the" include plural references unless the context clearly dictates otherwise. Conversely, it is contemplated that the claims may be drafted to exclude any optional element or be further limited using exclusive terminology as "solely," "only" and the like in connection with the recitation of claim elements or by use of a "negative" limitation. It is also contemplated that any optional feature of the inventive variations described herein may be set forth and claimed independently, or in combination with any one or more of the features described herein.

Although the foregoing specific details describe various embodiments of the invention, persons reasonably skilled in the art will recognize that various changes may be made in the details of the apparatus of this invention without departing from the spirit and scope of the invention as defined in the appended claims. Therefore, it should be understood that, unless otherwise specified, this invention is not to be limited to the specific details shown and described herein.

REFERENCES

Each of the following references is incorporated herein by reference in its entirety:

U.S. patent application Ser. No. 10/811,069 to Smith, filed Mar. 26, 2004.

Smith, B. D. (March 2005), *Reconstruction methods and completeness conditions for two Compton data models*, J. Opt. Soc. Am. A., vol. 22(3), pp. 445-459.

Smith, B. D. (1990), *Cone-beam tomography: recent advances and a tutorial review*. Opt. Eng'g, vol. 29(5), pp. 524-533.

Smith, B. D. (1987). *Computer-aided tomography imaging from cone-beam data*. Ph.D. thesis, University of Rhode Island.

Smith, B. D. (1985), *Image reconstruction from cone-beam projections: necessary and sufficient conditions and reconstruction methods*, IEEE Transactions on Medical Imaging, MI-4: 14-28.

Smith, K. T. et al. (1977). *Practical and mathematical aspects of the problem of reconstructing objects from radiographs*. Bull. Amer. Math. Soc., 83:1227-1270.

Parra, L. C. (Aug. 2000). *Reconstruction of cone-bam projections from Compton scattered data*. IEEE Transactions on Nuclear Science, vol. 47, no. 4, pp. 1543-1550.

Evans, B. L. et al. (1999). "Deconvolution of shift-variant broadening for Compton scatter imaging," *Nuclear Instruments and Methods in Physics Research A*, vol. 422, pp. 661-666.

Bracewell, R. N. (1978). *The Fourier Transform and its Applications*. McGraw-Hill, New York, N.Y.

Horn, B. K. P. (1978). *Density reconstruction using arbitrary ray-sampling schemes*. Proc. IEEE 66(5): 551-562.

Feller, W. (1968). *An introduction to probability theory and its applications*, vol. 1. New York: Wiley, 3 ed.

Gel'fand, I. M. and Shilov, G. E. (1964). *Generalized Functions: Volume 1 Properties and Operations*, volume 1. Academic Press, New York.

I claim:

1. A method of imaging a portion of a radioactive distribution, the method comprising:

selecting an imaging line through the radioactive distribution portion for which an approximation of an integral of radioactivity is to be derived;

providing a Compton camera instrument, including a Compton camera having a first detector and a second detector, wherein:

the first detector has a plurality of first detector elements distributed across three dimensions, each of the first detector elements being operable to scatter a photon interacting therewith;

the second detector has multiple second detector elements operable to detect the scattered photon;

the instrument is operable to record incidents in which a photon interacts with first and second detector elements;

the instrument being operable to record said incidents in a manner that preserves information enabling identification of the identities or relative positions of the first and second detector elements with which the photon interacted, and the approximate scatter angle of the photon; and there exists, for at least one given Compton camera position and orientation, a set of first and second detector elements that correspond to the imaging line, meaning that for at least one given Compton camera position and orientation, there exists on a plane perpendicular to the selected imaging line, a set of second detector elements numerously and angularly well-distributed around a coplanar first detector element such that segments connecting the first detector element of the set to at least two of the second detector elements of the set would form an angle of almost 180 degrees;

selecting a Compton camera relative position, relative orientation, and detector element set that corresponds to the imaging line;

implementing said selected Compton camera relative position, relative orientation, and detector element set to collect a data set of incidents of photons emanating from the radioactive distribution and interacting with the elements of the selected detector element set; and deriving from said data set an approximation of a line integral of the radioactivity along the imaging line.

2. The method of claim 1, wherein the first and second detectors are logical subsets of a single common physical detector.

3. The method of claim 1, wherein the first detector is a scatter detector and the second detector is an absorption detector.

4. The method of claim 1, wherein the deriving step includes applying the integral-of-cone-beam-line-integral model of Compton data image reconstruction to the collected data set to derive an approximation of a line integral of the radioactivity along the imaging line.

5. The method of claim 1, the method further comprising:
selecting a sufficient set of secondary lines parallel to, surrounding, and in the vicinity of the selected imaging line, to enable an approximation of a partial derivative;
for each said secondary line, selecting a Compton camera relative position, relative orientation, and detector element set that corresponds to the secondary line;
for each of said secondary lines, collecting a data set of incidents of photons emanating from the radioactive distribution interacting with the corresponding detector element set; and
wherein the deriving step includes applying a surface integral model of Compton data image reconstruction to the collected data sets for both the imaging line and the secondary lines to derive an approximation of a line integral of the radioactivity along the imaging line.

6. The method of claim 5, further comprising:
utilizing the same Compton camera relative orientation and detector element set corresponding to the imaging line to collect data sets for each of the said secondary lines, while varying only the relative position of the Compton camera in order to collect data sets for each of said secondary lines.

7. The method of claim 6, wherein the act of varying the relative position of the Compton camera with respect to the radioactive distribution is accomplished by moving the camera while keeping the radioactive distribution stationary.

8. The method of claim 6, wherein the act of varying the relative position of the Compton camera with respect to the radioactive distribution is accomplished by keeping the camera stationary while the radioactive distribution is moved.

9. The method of claim 6, wherein the act of varying the relative position of the Compton camera with respect to the radioactive distribution is accomplished by moving both the camera and the radioactive distribution.

10. The method of claim 5, further comprising:
providing a Compton camera instrument that has a sufficient number of first detector elements to enable selection of detector element sets that correspond to each of said secondary lines, without varying the relative position or orientation of the Compton camera with respect to the distribution; and utilizing a plurality of detector element sets to collect data sets for the imaging line and each of said secondary lines simultaneously.

11. The method of claim 1, applied to reconstructing a cross-section, the method further comprising:
selecting a cross-sectional portion of the radioactive distribution for reconstruction;
selecting a plurality of imaging lines that lie on a plane containing the selected cross-sectional portion and that are widely and numerously distributed through the selected cross-sectional portion;
for each said selected imaging line:
selecting a Compton camera relative position, relative orientation, and detector element set that corresponds to the imaging line;
implementing said selected Compton camera relative position, relative orientation, and detector element set to collect a data set of incidents of photons emanating from the radioactive distribution and interacting with the elements of the selected detector element set; and
deriving from said data set an approximation of an integral of the radioactivity along the imaging line; and
reconstructing from said multiple integral approximations a two-dimensional representation of the selected radioactive distribution cross-sectional portion.

12. The method of claim 11, wherein the implementation of said selected Compton camera relative positions, relative orientations, and detector element sets includes moving the camera through multiple points on at least a half-circle trajectory around the radioactive distribution.

13. The method of claim 11, wherein the implementation of said selected Compton camera relative positions, relative orientations, and detector element sets includes rotating the radioactive distribution through at least 180 degrees.

14. The method of claim 11,
wherein the implementation of said selected Compton camera relative position, relative orientation, and detector element sets include selecting multiple points surrounding the selected radioactive distribution cross-sectional portion;
said multiple selected points lying along a plurality of tangential segments to a semicircular trajectory around the radioactive distribution;
wherein said tangential segments are distributed around said semicircular trajectory; and
wherein each tangential segment spans a projection of the selected cross-sectional portion onto the tangential segment; and
traversing said camera through said multiple selected points.

15. The method of claim 12, wherein at each of said multiple points along the half-circle trajectory, the camera is relatively re-oriented at multiple angular orientations with respect to the radioactive distribution to provide measurements of multiple imaging lines that fan out from said point across the entire extent of the cross-sectional portion of the radioactive distribution to be reconstructed.

16. The method of claim 1, applied to reconstructing a volume, the method further comprising:
selecting a volumetric portion of the radioactive distribution for reconstruction;
selecting a plurality of imaging lines that are widely and numerously distributed through and about the vicinity of the selected volumetric portion;
for each said selected imaging line:

selecting a Compton camera relative position, relative orientation, and detector element set that corresponds to the imaging line;

implementing said selected Compton camera relative position, relative orientation, and detector element set to collect a data set of incidents of photons emanating from the radioactive distribution and interacting with the elements of the selected detector element set; and deriving from said data set an approximation of an integral of the radioactivity along the imaging line; and reconstructing from said multiple integral approximations a three-dimensional representation of the selected volumetric portion.

17. The method of claim 16, wherein the implementation of said selected Compton camera relative positions, relative orientations, and detector element sets comprises:

advancing the camera through multiple arc points along at least a half-circle trajectory around the selected volumetric portion; and at each said arc point, moving the camera in a raster fashion across a rectangular raster-coverage portion of a tangent plane to the arc point, said tangent plane being parallel to a longitudinal axis of the half circle trajectory;

for each tangent plane, the corresponding rectangular raster-coverage portion completely enclosing a projection of the selected volumetric portion onto the tangent plane.

18. The method of claim 1, applied to reconstructing a parallel projection, the method further comprising:

selecting a plurality of parallel imaging lines from which a parallel projection of the radioactive distribution is to be reconstructed;

for each said selected imaging line:
selecting a Compton camera relative position, relative orientation, and detector element set that corresponds to the imaging line;

implementing said selected Compton camera relative position, relative orientation, and detector element set to collect a data set of incidents of photons emanating from the radioactive distribution and interacting with the elements of the selected detector element set; and deriving from said data set an approximation of an integral of the radioactivity along the imaging line; and reconstructing from said multiple integral approximations a representation of the parallel projection of the radioactive distribution.

19. The method of claim 18, wherein the selected parallel imaging lines are widely and numerously distributed in two dimensions.

20. The method of claim 19, wherein implementation of said selected Compton camera relative positions, relative orientations, and detector element sets include moving the camera in a raster fashion across a rectangular raster-coverage portion that completely encloses the parallel projection.

21. The method of claim 1, applied to reconstructing a cone beam projection, the method further comprising:

selecting multiple focal points within the radioactive distribution;

for each said focal point, selecting a plurality of converging imaging lines that
converge on the focal point;
for each converging imaging line:
selecting a Compton camera relative position, relative orientation, and detector element set that corresponds to the imaging line;
implementing said selected Compton camera relative position, relative orientation, and detector element set to collect a data set of incidents of photons emanating from the radioactive distribution and interacting with the elements of the selected detector element set; and deriving from said data set an approximation of an integral of the radioactivity along the imaging line; and for each focal point, reconstructing from said multiple integral approximations an aggregative representation of the radioactivity detected along the corresponding set of converging imaging lines; and comparing the representations of aggregative representations of radioactivity for different focal points to identify points of relatively greater radioactivity.

22. The method of claim 21, wherein said selected multiple focal points lie on one of plurality of parallel imaging lines from which a parallel projection of the radioactive distribution has previously been reconstructed in accordance with the following steps:

selecting a plurality of parallel imaging lines from which a parallel projection of the radioactive distribution is to be reconstructed;

for each said selected imaging line:
selecting a Compton camera relative position, relative orientation, and detector element set that corresponds to the imaging line;
implementing said selected Compton camera relative position, relative orientation, and detector element set to collect a data set of incidents of photons emanating from the radioactive distribution and interacting with the elements of the selected detector element set; and deriving from said data set an approximation of an integral of the radioactivity along the imaging line; and reconstructing from said multiple integral approximations a representation of the parallel projection of the radioactive distribution.

23. The method of claim 22, wherein both the parallel projection and cone beam projection reconstructions are performed using a common data superset of previously recorded incidents.

24. The method of claim 23, wherein the common data superset of recorded incidents is obtained without changing the relative position or relative orientation of the Compton camera with respect to the radioactive distribution, and wherein different detector element sets of the Compton camera are selected to collect the data sets for the imaging lines used to perform the parallel projection and cone beam projection reconstructions.

25. The method of claim 22, further comprising:

using said reconstruction of a parallel projection of the radioactive distribution to identify a section, along one of said plurality of parallel imaging lines, of the radioactive distribution having relatively greater radioactivity; and using said reconstruction of a cone beam projection of the radioactive distribution to identify a point along the identified parallel imaging line having relatively greater radioactivity than other points along the identified parallel imaging line;

whereby hot spots in a radioactive distribution are identified using a combination of parallel and cone beam projection reconstructions.

26. The method of claim 25, wherein the radioactive distribution is contained within a cargo container, the method farther comprising:

using said reconstructions to identify radioactive hot spots in said cargo container.

27. The method of claim 1, wherein the first detector has multiple first detector elements distributed in three dimensions across a first cone-shaped surface and the second detector has multiple second detector elements distributed in three dimensions across a second cone-shaped surface that surrounds the first cone-shaped surface.

28. The method of claim 27, wherein the first and second detectors are concentric and share a common axis of symmetry, a portion of a plane perpendicular to said axis of symmetry defining a face of the camera.

29. The method of claim 28, wherein the second cone-shaped surface resembles a truncated cone, such that for every detector element on the second detector, there is at least one coplanar detector element on the first detector lying on a plane perpendicular to the common axis of symmetry.

30. The method of claim 28, applied to local reconstruction of a selected volume within a patient, wherein the camera face is oriented parallel to a longitudinal axis of the patient, and wherein the first detector spans an area, perpendicular to the detectors' common axis of symmetry, that exceeds the selected volume's width along the patient's longitudinal axis, the method further comprising:
  moving the camera along at least a semi-elliptical trajectory, perpendicular to the patient's longitudinal axis, around the patient, while maintaining a camera face orientation that is parallel to the patient's longitudinal axis and perpendicular to a plane containing the semi-elliptical trajectory;
  collecting data sets of incidents of photons emanating from the patient at each of multiple points along the at least a semi-elliptical trajectory;
  deriving from said data sets approximations of integrals of radioactivity along imaging lines that are widely and numerously distributed through and about the vicinity of the selected volume; and
  reconstructing from said multiple integral approximations a three-dimensional representation of the radioactivity in the selected volume.

31. The method of claim 28, applied to celestial imaging, wherein the camera face is oriented perpendicular to a celestial source axis line intersecting the Compton camera and an apparent position of the celestial source; the celestial source axis line constituting an imaging line along which an approximation of an integral of radioactivity is derived.

32. The method of claim 31, further comprising reconstructing a distribution of radiation of the celestial source as a function of the celestial source's radius, wherein the reconstructed distribution reflects an assumption that the celestial source is spherically symmetric.

33. The method of claim 27, wherein the first detector elements are distributed across the first cone-shaped surface in a manner resembling grids on a piece of engineering graph paper twisted into the shape of a cone; and the second detector elements are distributed across the second cone-shaped surface in a manner resembling grids on a piece of engineering graph paper twisted into the shape of a truncated cone.

34. The method of claim 1, wherein the first detector has multiple first detector elements distributed in three dimensions across a first hemispherically-shaped surface and the second detector has multiple second detector elements distributed in three dimensions across a second hemispherically-shaped surface that surrounds the first hemispherically-shaped surface.

35. The method of claim 16, wherein the implementation of said selected Compton camera relative positions, relative orientations, and detector element sets include moving the Compton camera along a saddle-shaped trajectory around the distribution to be imaged.

36. The method of claim 16, wherein the implementation of said selected Compton camera relative positions, relative orientations, and detector element sets include adjusting the relative position of the Compton camera with the radioactive distribution along a spiral trajectory around the distribution to be imaged.

37. The method of claim 36, wherein the act of adjusting the relative position of the Compton camera with the radioactive distribution along a spiral trajectory involves rotating the Compton camera in a circular trajectory and advancing the radioactive distribution along an axial direction.

38. The method of claim 1, wherein the Compton camera instrument has second detector elements that are widely and numerously distributed on opposite sides of a coplanar first detector element; the method further comprising:
  pairing the second detector elements of a selected detector element set with the coplanar first detector element to form measurement bins, wherein measurement bins associated with second detector elements on opposite sides of the coplanar first detector element collect redundant data;
  for some redundant pairs of measurement bins in which one of the bins of the redundant pair collects small scatter data and the other of bins of the redundant pair collects large scatter data, blending the data from the redundant pair to compensate for a Klein-Nishina distribution of scatter angles and to improve accuracy.

39. The method of claim 16, wherein the selected plurality of imaging lines lie on parallel planes that intersect the selected volumetric portion; and wherein the three-dimensional representation is reconstructed using multiple integral approximations only along imaging lines that lie on said parallel planes.

40. The method of claim 16, wherein:
  a first set of the selected plurality of imaging lines lie on a parallel projection that passes through the selected volumetric portion at a first angle;
  a second set of the selected plurality of imaging lines lie on a parallel projection that passes through the selected volumetric portion at a second angle;
  the first angle is not equal to the second angle;
  each of the first and second sets of imaging lines is sufficiently widely and numerously distributed to enable reconstruction of a three-dimensional representation of the selected volumetric portion; and
  to improve the quality of the reconstructed representation, the reconstruction of the three-dimensional representation of the selected volumetric portion uses multiple integral approximations from both the first and second sets.

41. The method of claim 40, as applied to local reconstruction of a section of the distribution, wherein the first angle is 90 degrees and the second angle is sufficiently large so that substantially none of the second set of imaging lines intersect portions of the distribution outside the section to be locally reconstructed.

42. The method of claim 41, wherein the section of the distribution to be locally reconstructed comprises a patient's head.

43. The method of claim 1, wherein the derivation step includes numerically solving a set of simultaneous equations that relate the integral of radioactivity along the imaging line to the data of the data set.

44. The method of claim 1, wherein the radioactivity of the distribution is generated, at least in part, by a beam of neutrons penetrating the distribution.

45. The method of claim 44, wherein the distribution is contained within a container.

46. The method of claim 1, further comprising simultaneously using another device that is operable to sense a qualitatively different type of phenomenon, not directly perceptible by human senses, regarding the distribution, in order to detect the likely presence of materials operable to shield nuclear material.

47. The method of claim 46, wherein the other device is a cosmic ray muon imaging device.

48. An apparatus for imaging a portion of a radioactive distribution, the apparatus comprising a Compton camera instrument as set forth in claim 1, the apparatus being further operable to:
  select or enable user selection of an imaging line through the radioactive distribution portion for which an approximation of an integral of radioactivity is to be derived;
  select a Compton camera relative position, relative orientation, and detector element set that corresponds to the imaging line;
  implement said selected Compton camera relative position, relative orientation, and detector element set to collect a data set of incidents of photons emanating from the radioactive distribution and interacting with the elements of the selected detector element set; and
  derive from said data set an approximation of an integral of the radioactivity along the imaging line.

49. The apparatus of claim 48, wherein the first detector has multiple first detector elements distributed in three dimensions across a first cone-shaped surface and the second detector has multiple second detector elements distributed in three dimensions across a second cone-shaped surface that surrounds the first cone-shaped surface.

50. The apparatus of claim 48, further comprising a frame for advancing the Compton camera through a trajectory.

51. A method of imaging a far field source, the method comprising:

(a) providing a Compton camera instrument, including a Compton camera having a planar first detector and a planar second detector, the first detector being parallel to the second detector, wherein:
  the first detector has a plurality of first detector elements operable to scatter a photon interacting with a first detector element;
  the second detector has a plurality of second detector elements operable to detect the scattered photon;
  the instrument is operable to record incidents in which a photon interacts with first and second detector elements; and
  the instrument being operable to record said incidents in a manner that preserves information enabling identification of the identities or relative positions of the first and second detector elements with which the photon interacted, and the approximate scatter angle of the photon;
(b) orienting the Compton camera at a selected acute angle, of between 10 and 80 degrees, to a far field source axis line intersecting the Compton camera and an apparent position of the far field source;
(c) selecting a set of first and second detector elements lying on a common plane perpendicular to the far field axis line;
(d) using said selected detector element set to collect data of incidents of photons interacting with the elements of the selected detector element set;
(e) rotating the Compton camera through multiple points around the far field axis line while maintaining the previously selected acute angle of the Compton camera to the far field axis line;
(f) at each of said points, repeating steps (c)-(d); and
(g) deriving from said data set an approximation of an integral of the radioactivity along the far field axis line.

52. The method of claim 51, wherein the far field source is a celestial object.

53. The method of claim 51, wherein the far field source is a nuclear device.

* * * * *